(12) United States Patent
Richard et al.

(10) Patent No.: US 8,535,702 B2
(45) Date of Patent: Sep. 17, 2013

(54) MEDICAL DEVICES HAVING POROUS POLYMERIC REGIONS FOR CONTROLLED DRUG DELIVERY AND REGULATED BIOCOMPATIBILITY

(75) Inventors: Robert E. Richard, Wrentham, MA (US); Frederick H. Strickler, Natick, MA (US); Marlene C. Schwarz, Auburndale, MA (US); Rudolf Faust, Lexington, MA (US); Shrirang V. Ranade, Arlington, MA (US); Michael N. Helmus, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2004 days.

(21) Appl. No.: 11/048,616

(22) Filed: Feb. 1, 2005

(65) Prior Publication Data

US 2006/0171985 A1  Aug. 3, 2006

(51) Int. Cl.
*A61F 2/00* (2006.01)

(52) U.S. Cl.
USPC ........... 424/423; 424/426; 525/224; 525/242; 525/309; 604/96.01; 604/890.1; 604/891.1

(58) Field of Classification Search
None
See application file for complete search history.

(56) References Cited

U.S. PATENT DOCUMENTS

| | | | |
|---|---|---|---|
| 5,447,724 A | 9/1995 | Helmus et al. | 424/426 |
| 5,569,463 A | 10/1996 | Helmus et al. | 424/426 |
| 5,733,925 A | 3/1998 | Kunz et al. | 514/449 |
| 5,738,902 A | 4/1998 | Forrestal et al. | 427/2.12 |
| 6,337,198 B1 | 1/2002 | Levene et al. | 435/174 |
| 6,653,358 B2 | 11/2003 | Bruza et al. | 521/77 |
| 6,979,473 B2 * | 12/2005 | O'Connor et al. | 427/2.24 |
| 7,771,740 B2 * | 8/2010 | Strickler et al. | 424/423 |
| 2001/0009688 A1 | 7/2001 | Dinh et al. | 427/2.1 |
| 2002/0055239 A1 | 5/2002 | Tuominen et al. | 438/466 |
| 2002/0055710 A1 | 5/2002 | Tuch | 604/103.02 |
| 2002/0103538 A1 | 8/2002 | Hughes et al. | 623/6.59 |
| 2002/0107330 A1 | 8/2002 | Pinchuk et al. | 525/242 |
| 2002/0111667 A1 | 8/2002 | Girton et al. | 623/1.13 |
| 2002/0138154 A1 | 9/2002 | Li et al. | 623/66.1 |
| 2002/0151796 A1 | 10/2002 | Koulik | 600/458 |
| 2002/0187288 A1 | 12/2002 | Lim et al. | 428/35.2 |
| 2003/0073158 A1 | 4/2003 | Ma | 435/68.1 |
| 2003/0125803 A1 | 7/2003 | Vallana et al. | 623/1.42 |
| 2003/0165625 A1 | 9/2003 | So et al. | 427/385.5 |
| 2003/0208259 A1 | 11/2003 | Penhasi | 623/1.15 |
| 2003/0216806 A1 | 11/2003 | Togawa et al. | 623/1.15 |
| 2003/0222048 A1 | 12/2003 | Asakawa et al. | 216/2 |
| 2003/0235602 A1 | 12/2003 | Schwarz | 424/424 |
| 2003/0235603 A1 | 12/2003 | Schwarz et al. | 424/426 |
| 2003/0236320 A1 | 12/2003 | Martin et al. | 523/124 |
| 2003/0236513 A1 | 12/2003 | Schwarz et al. | 604/890.1 |
| 2004/0028875 A1 | 2/2004 | Van Rijn et al. | 428/98 |
| 2004/0106987 A1 | 6/2004 | Palasis et al. | 623/1.42 |
| 2006/0193892 A1 * | 8/2006 | Furst et al. | 424/426 |

FOREIGN PATENT DOCUMENTS

| | | |
|---|---|---|
| WO | 96/10428 | 4/1996 |
| WO | 9618498 | 6/1996 |
| WO | WO 97/04809 | 2/1997 |
| WO | WO 00/01322 | 1/2000 |
| WO | 02/074356 | 9/2002 |
| WO | 03/063924 | 8/2003 |

OTHER PUBLICATIONS

Tejal A. Desai, et al., "Characterization of Micromachined Silicon Membranes for Immunoisolation and Bioseparation Applications", *J. Membrane Science*, 159 (1999) 221-231.
Moon Suk Kim, et al., "Novel synthesis of poly(ethyleneglycol-b-ε-caprolactone) block copolymers," The 227th ACS National Meeting, Anaheim, CA, Polymer Characterization and Synthesis, Paper No. 215, Mar. 28, 2004, abstract only, 1 page. http://oasys2.confex.com/acs/227nm/techprogram/P728726.HTM.
Pathiraja A. Gunatillake, et al., "Biodegradable Synthetic Polymers for Tissue Engineering", *European Cells and Material*, vol. 5, 2003, pp. 1-16. http://www.ecmjournal.org/journal/papers/vol005/pdf/v005a01.pdf.
M.N. Helmus, et al. "Plasma Interaction on Block Copolymers as Determined by Platelet Adhesion" *Adv. Chem. Series No. 199*, S. L. Cooper et al., Eds., 1982, pp. 81-93.
Shastri, et al., "In Situ Pore Formation in a Polymer Matrix by Differential Polymer Degradation", *Biomaterial*, 24 (2003), pp. 3133-3137.
J.C. Cho, et al. "Synthesis, Characterization, and Drug Release Properties of Poly(ε-caprolactone-b-isobutylene-b-ε-caprolactone)" *Polymeric Materials: Science and Engineering Preprints* (2005), 92, pp. 664-665.
M.S. Kim, et al., "Synthesis of Poly(ε-caprolactone-isobutylene) block- and Poly(ε-caprolactone-isobutylene-ε-caprolactone) Triblock Copolymer," *Polymer Bulletin* (Berlin, Germany) (2002), 48(2), pp. 127-134.
Sipos, L., et al. "Synthesis of poly(L-lactide)-block-polyisobutylene-block-poly(L-lactide), A New Biodegradable Thermoplastic Elastomer," *Macromol. Chem. Rapid Commun.* 1995, 16, pp. 935-940.
Prince Antony, et al., "Atomic Force Microscopic Studies of Novel Arborescent Block and Linear Triblock Polystyrene-Polyisobutylene Copolymers", *European Polymer Journal*, 40 (2004), pp. 149-157.

\* cited by examiner

*Primary Examiner* — Hasan Ahmed
(74) *Attorney, Agent, or Firm* — Mayer & Williams PC; David B. Bonham

(57) ABSTRACT

The present invention relates to phase separated polymeric regions and to their use in conjunction with implantable or insertable medical devices. In some aspects of the invention, phase separated polymeric regions are provided that include (a) at least one biostable polymeric phase and (b) at least one biodisintegrable polymeric phase, which is of nanoscale dimensions and which undergoes biodisintegration such that the phase separated polymeric region becomes a nanoporous polymeric region in vivo. Other aspects of the invention are directed to methods of making implantable or insertable medical devices having at least one nanoporous polymeric region. These methods include (a) providing a phase separated polymeric region comprising a stable polymeric phase and a disintegrable polymeric phase of nanoscale dimensions, (b) selectively removing the disintegrable polymeric phase thereby producing the nanoporous polymeric region. In still other aspects, implantable or insertable medical devices are provided which have phase separated polymeric regions that include (a) at least one block copolymer having at least one biostable polymer block and at least one biodisintegrable polymer block and (b) at least one therapeutic agent which is released in vivo upon implantation or insertion of the medical device.

57 Claims, 7 Drawing Sheets

MEDICAL DEVICES HAVING POROUS POLYMERIC REGIONS FOR CONTROLLED DRUG DELIVERY AND REGULATED BIOCOMPATIBILITY

TECHNICAL FIELD

This invention relates to medical devices having porous polymeric regions that can, for example, control drug delivery and/or regulate tissue biocompatibility.

BACKGROUND OF THE INVENTION

The in vivo presentation and/or delivery of a biologically active agent within the body of a patient is common in the practice of modern medicine. In vivo presentation and/or delivery of biologically active agents is often implemented using medical devices that may be temporarily or permanently placed at a target site within the body. These medical devices can be maintained, as required, at their target sites for short or prolonged periods of time, in order to present and/or deliver biologically active agent at the target site.

For example, numerous polymer-based medical devices have been developed for the delivery of therapeutic agents to the body. Examples include drug eluting coronary stents which are commercially available from Boston Scientific Corp. (TAXUS), Johnson & Johnson (CYPHER), and others. In accordance with some typical delivery strategies, a therapeutic agent is provided within or beneath a biostable or biodegradable polymeric layer that is associated with a medical device. Once the medical device is placed at the desired location within a patient, the therapeutic agent is released from the medical device at a rate that is dependent, for example, upon the loading of the therapeutic agent and upon the nature of the polymeric layer.

For example, controlling the rate of therapeutic agent release and the overall dose are key parameters for proper treatment in many cases. Selection of the polymeric layer will have a great impact on these parameters. In many formulations, the thickness of the layer can be changed to control the total dose. However, control of the amount of therapeutic agent released in a specific time interval (e.g., the rate of release) presents greater challenges. The rate of release is generally a function of the material properties of the polymeric layer. Moreover, in many instances, the therapeutic agent becomes trapped in the release layer, never to be released.

It is also known that porous surfaces, including nanoporous surfaces can directly interact with cell receptors, thereby controlling the adhesion or non-adhesion of cells to the surface.

SUMMARY OF THE INVENTION

The present invention relates to phase separated polymeric regions and to their use in conjunction with implantable or insertable medical devices.

In some aspects of the invention, phase separated polymeric regions are provided that include (a) at least one biostable polymeric phase and (b) at least one biodisintegrable polymeric phase, which is of nanoscale dimensions and which undergoes biodisintegration such that the phase separated polymeric region becomes a nanoporous polymeric region in vivo.

Other aspects of the invention are directed to methods of making implantable or insertable medical devices having at least one nanoporous polymeric region. The methods include (a) providing a phase separated polymeric region comprising a stable polymeric phase and a disintegrable polymeric phase of nanoscale dimensions, (b) selectively removing the disintegrable polymeric phase thereby producing the nanoporous polymeric region.

In still other aspects, implantable or insertable medical devices are provided which have phase separated polymeric regions that include (a) at least one block copolymer having at least one biostable polymer block and at least one biodisintegrable polymer block and (b) at least one therapeutic agent which is released in vivo upon implantation or insertion of the medical device.

An advantage of the present invention is that medical devices can be provided, in which porous polymeric regions are provided, either in vivo or ex vivo.

Consequently, medical devices can be provided which have controlled biologic interactions. For example, medical devices can be provided in accordance with the present invention that contain porous polymeric regions, the pore size of which can be optimized to regulate tissue ingrowth and/or the adhesion of cells thereto.

Moreover, medical devices can be provided which release biologically active agents after administration to a patient. For example, medical devices can be provided in accordance with the present invention, in which a therapeutic agent is provided within or beneath a region having pores which are formed ex vivo under controlled conditions. As another example, medical devices can be provided in accordance with the present invention, which contain phase separated polymeric regions that can undergo degradation or hydration under biological conditions to deliver therapeutic agents that are provided within or beneath the polymeric regions.

The release profile (including the release rate and cumulative release as a function of time) can be tuned in these embodiments, for instance, by proper selection of the polymeric blocks making up the polymeric regions. For example, the release profile can be tuned by the proper selection of the monomeric constituents making up the various polymeric blocks within the polymeric regions, the molecular weights of the various polymeric blocks, the relative amounts of the various polymeric blocks, and so forth (which parameters can affect, for example, the polarity, degradation characteristics, etc., of the polymeric regions).

In addition, medical devices can be provided in accordance with the present invention that contain polymeric coatings with mechanical properties that permit the devices to undergo dimensional changes without compromising the integrity of the coatings.

These and many other embodiments and advantages of the present invention will become immediately apparent to those of ordinary skill in the art upon review of the Detailed Description and Claims to follow.

DETAILED DESCRIPTION

Figure 1:
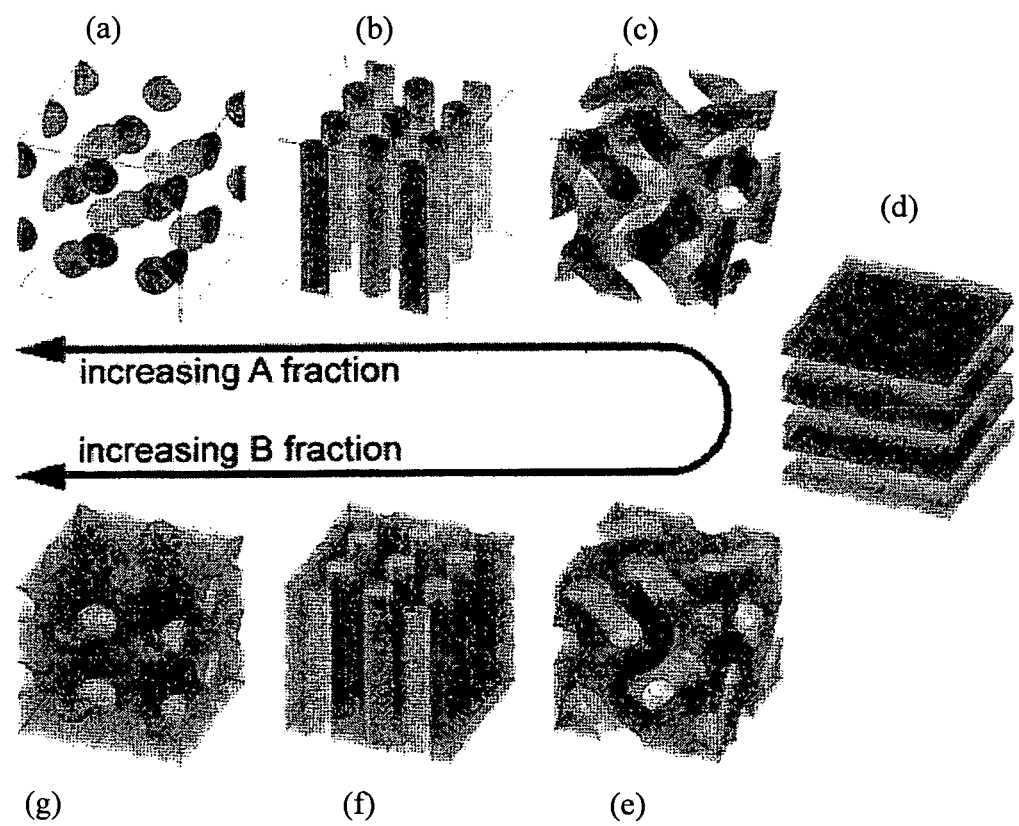
FIG. 1 is an illustration of a series of idealized morphologies of a polymeric region which contains two polymeric phases.

The present invention relates to phase separated polymeric regions and to their use in conjunction with implantable or insertable medical devices.

In some aspects of the invention, phase separated polymeric regions are provided that include (a) at least one biostable polymeric phase and (b) at least one biodisintegrable polymeric phase, which is of nanoscale dimensions and which undergoes biodisintegration such that the phase separated polymeric region becomes a nanoporous polymeric region in vivo.

Other aspects of the invention are directed to methods of making implantable or insertable medical devices having at least one nanoporous polymeric region. The methods include (a) providing a phase separated polymeric region comprising a stable polymeric phase and a disintegrable polymeric phase of nanoscale dimensions, (b) selectively removing the disintegrable polymeric phase thereby producing the nanoporous polymeric region.

In still other aspects, implantable or insertable medical devices are provided which have phase separated polymeric regions that include (a) at least one block copolymer having at least one biostable polymer block and at least one biodisintegrable polymer block and (b) at least one therapeutic agent which is released in vivo upon implantation or insertion of the medical device.

Polymeric regions for use in conjunction with the present invention can correspond, for example, to an entire device (e.g., a stent, a graft or a tissue engineering scaffold), or they can correspond to only a portion of a medical device (e.g., an interwoven fiber or a coating layer overlying a medical device substrate).

As used herein a "polymeric region" is region that contains one or more polymers, typically 50 wt % or more polymers. A "polymeric phase" is a phase (sometimes referred to as a "phase domain") that comprises one or more miscible polymers (e.g., homopolymers, periodic, random, statistical or gradient copolymers, etc.), one or more miscible polymer portions (e.g., polymer blocks of block copolymers), or a combination of one or more miscible polymers and one or more miscible polymer portions. Hence, as discussed further below, the stable and disintegrable polymeric phases of the phase separated polymeric regions of the present invention are provided in some embodiments using a single polymer (e.g., a block copolymer with at least one stable block and at least one disintegrable block that is immiscible with the stable block), or they can be provided in other embodiments using two or more polymers (e.g., a blend of immiscible homopolymers, a blend of immiscible copolymers, a blend of immiscible homopolymers and copolymers, and so forth).

In some embodiments of the present invention, the disintegrable polymeric phases are removed from the stable polymeric phases by subjecting the phase separated polymeric regions to conditions whereby the disintegrable polymeric phases are selectively removed from stable polymeric phases. For example, the disintegrable polymeric phases may be removed by melting, sublimation, dissolution, chemical breakdown (including enzymatic breakdown, hydrolysis, various other in vivo biological actions, ozonolysis, oxidation, radiation breakdown, pyrolysis, and so forth) or a combination thereof. Accordingly, examples of conditions which can be used to selectively remove the disintegrable polymeric phases include both in vivo and ex vivo conditions, such as exposure to elevated temperatures that are effective to melt, sublime or break down the disintegrable polymeric phases, exposure to aqueous and/or organic solvents (including biological fluids) at temperatures and pressures that are effective to dissolve the disintegrable polymeric phases, exposure to reactive chemical species (including biological fluids) at concentrations, temperatures and pressures that are effective to degrade the disintegrable polymeric phases, exposure to radiation doses effective to degrade the disintegrable polymeric phases, and so forth.

In certain embodiments, phase separated polymeric regions are provided which contain at least one biostable polymeric phase and at least one biodisintegrable polymeric phase. By "biodisintegrable polymeric phase" is meant that the polymeric phase undergoes dissolution, degradation (i.e., bond cleavage, such as hydrolysis) and/or other disintegration process during the time over which the medical device is designed to reside in the body. Similarly, by "biostable" is meant that the polymeric phase remains substantially intact during the time over which the medical device is designed to reside in the body.

It is noted that, in some embodiments, block copolymers, which contain one or more dissolvable polymer blocks (e.g., polyethylene oxide) covalently bound to one or more hydrophobic biostable polymer blocks (e.g., polystyrene and/or polyisobutylene), are blended with at least one other biostable polymer. If the hydrophobic biostable blocks of the block copolymer are small relative to the dissolvable blocks, then the block copolymer may be soluble and pores may form. On the other hand, if the hydrophobic biostable blocks are large relative to the dissolvable blocks, then the copolymer may not dissolve in vivo, and pore will not be formed. Nonetheless, the presence of block copolymers having such dissolvable blocks, which hydrate in vivo upon exposure to biological fluids, typically has an influence upon the release characteristics of the polymeric regions of which they are a part.

In many embodiments, the phase separated polymeric regions of the invention contain at least one disintegrable polymeric phase that is of nanoscale dimensions. By saying that a disintegrable polymeric phase is of "nanoscale dimensions" is meant that the disintegrable polymeric phase has at least one dimension (for instance, the diameter of a sphere, the diameter of a cylinder, the thickness of a sheet or ribbon, etc.) that is 100 nm or less in length, frequently 50 nm or less in length, 25 nm or less in length, 10 nm or less in length, or even 5 nm or less in length. Commonly the disintegrable polymeric phase will have at least two orthogonal (i.e., perpendicular) dimensions that do not exceed 100 nm. The disintegrable polymeric phase will also commonly have regions with one, two, or even three orthogonal dimensions that are larger than 100 nm in length.

Phase separated polymeric compositions may display a wide variety of phase configurations. For example, FIG. 1 illustrates some typical idealized phase morphologies for a polymeric region which contains two polymeric phases, one shown in lighter shading (phase A) and the other shown in darker shading (phase B). As the fraction of phase A relative to phase B goes from high to low, morphologies commonly encountered are: (a) spheres of phase B in a matrix of phase A, (b) cylinders of phase B in a matrix of phase A, (c) dual labyrinths of phase B in phase A, which is a co-continuous (i.e., bi-continuous) system, (d) alternating lamellae of phase A and phase B, (e) dual labyrinths of phase A in phase B, another co-continuous system, (f) cylinders of phase A in a matrix of phase B, and (g) spheres of phase A in a matrix of phase B.

If the multi-phase system is of an appropriate configuration, and if the disintegrable polymeric phase is removed either in vivo or ex vivo, a porous polymeric region is left behind. For example, assuming that phase A in FIG. 1 is a disintegrable polymeric phase and that phase B is a stable polymeric phase, upon removal of phase A, porous polymeric regions are produced that correspond, for example, to the following: a region containing an interconnected network of pores (see, configuration "e" of FIG. 1), a region containing a series of parallel cylindrical pores (see, configuration "f" of FIG. 1), and a region containing isolated spherical pores (see, configuration "g" of FIG. 1), among many other possible configurations. Of these configurations, configuration "e" is preferred in some instance, because it is a bi-continuous structure (i.e., it is a structure in which phase A and phase B each extends from one side of the polymeric region to another) and is therefore capable of producing a polymeric region having a network of interconnected pores that extend throughout the polymeric region.

As used herein, a "nanoporous" region is one that contains nanopores. In the present invention, nanopores are formed by removal of a disintegrable polymeric phase that is of nanoscale dimensions. Hence, analogous to the above, a "nanopore" is a void having at least one dimension that does not exceed 100 nm in length. Commonly, a nanopore will have at least two orthogonal (i.e., perpendicular) dimensions that do not exceed 100 nm. Nanoporous regions will also commonly contain pores with one, two, or even three orthogonal dimensions that are greater than 100 nm.

Porous regions can have various interesting properties.

For example, it is known that nanostructured surfaces, including nanoporous surfaces, can directly interact with cell receptors, thereby controlling the adhesion or non-adhesion of cells and tissues to the surface.

As another example, in some embodiments, nanoporous polymeric regions are produced in which the lateral dimensions (e.g., the diameter, for an idealized, cylindrical pore) of the nanopores approach the lateral dimensions (e.g., the hydrated diameter) of a biologically active agent that is to be released. Consequently, the therapeutic agent can move within, and ultimately be released from, pores of these diameters (as opposed to being trapped by pores having smaller diameters). Moreover, the interactions between the biologically active agent and the walls of the nanopores are expected to have a significant effect upon the release profile that is observed. Indeed, as the diameter of the pore approaches the diameter of the agent to be delivered, the surface interactions begin to dominate release rates. See, e.g., Tejal A. Desai, Derek Hansford, "Mauro Ferrari Characterization of micromachined silicon membranes for immunoisolation and bioseparation applications J. Membrane Science," 159 (1999) 221-231, which describes insulin release through silicon nanomembranes. Although typically less regular than the parallel pore structures of nanoporous silicon membranes, the porous polymeric regions of the present invention are nonetheless expected to release therapeutic agents in a manner that is highly controlled, and have the potential to approach zero order release kinetics. The amount of biologically active agent released and the duration of that release are also affected by the depth and tortuousity of the pores within the porous polymeric region.

Pores that are not nanopores are also known to have useful properties. For example, tissue ingrowth is known to occur at porous surfaces of implanted devices (e.g., those with diameters on the order of microns), which may also be desirable to improve compatibility with body tissues, and limit rejection of the device.

As indicated above, the polymeric regions of the present invention can be provided in a wide variety of forms. For example, a polymeric region can be provided which corresponds to an entire medical device or to a portion of a medical device. For instance, the polymeric region can be in the form of one or more fibers which are incorporated into the medical device; or a polymeric layer can be formed over all or only a portion of an underlying medical device substrate; or a polymeric layer can be preformed and attached to an underlying medical device substrate.

Polymeric layers in accordance with the present invention can be provided over an underlying substrate at a variety of locations and in a variety of shapes, and they can be formed from a variety of polymeric materials. Materials for use as underlying medical device substrates include ceramic, metallic and polymeric substrates. The substrate material can also be a semiconductor (e.g., silicon or carbon). As used herein a "layer" of a given material is a region of that material whose thickness is small compared to both its length and width. As used herein a layer need not be planar, for example, taking on the contours of an underlying substrate. Layers can be discontinuous (e.g., patterned). Terms such as "film," "layer" and "coating" may be used interchangeably herein.

Hence, one or more polymeric regions can be provided on the medical device surface at desired locations and/or in desired shapes (e.g., in desired patterns, for instance, using appropriate masking techniques, including lithographic techniques). For example, for tubular devices such as stents (which can comprise, for example, a laser or mechanically cut tube, one or more braided, woven, or knitted filaments, etc), polymeric regions can be provided on the luminal surfaces, on the abluminal surfaces, on the lateral surfaces between the luminal and abluminal surfaces, patterned along the luminal or abluminal length of the devices, on the ends, and so forth. Moreover, multiple polymeric regions can be formed using the same or different techniques and they can contain no therapeutic agent, the same therapeutic agent, or different therapeutic agents as described further below. It is therefore possible, for example, to release the same or different therapeutic agents at different rates from different locations on the medical device. As another example, it is possible to provide a tubular medical device (e.g., a vascular stent) having a first region comprising a first therapeutic agent (e.g., an antithrombotic agent) on its inner, luminal surface and a second region comprising a second therapeutic agent that differs from the first therapeutic agent (e.g., an antiproliferative agent) on its outer, abluminal surface (as well as on the ends).

Examples of medical devices to which the present invention is applicable include various implantable and insertable medical devices, for example, catheters (e.g., renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, myocardial plugs, patches, pacemakers and pacemaker leads, heart valves, vascular valves, biopsy devices, patches for delivery of therapeutic agent to intact skin and broken skin (including wounds); tissue engineering scaffolds for cartilage, bone, skin and other in vivo tissue regeneration; sutures, suture anchors, anastomosis clips and rings, tissue staples and ligating clips at surgical sites; orthopedic fixation devices such as interference screws in the ankle, knee, and hand areas, tacks for ligament attachment and meniscal repair, rods and pins for fracture fixation, screws and plates for craniomaxillofacial repair; dental devices such as void fillers following tooth extraction and guided-tissue-regeneration membrane films following periodontal surgery; and various coated substrates that are implanted or inserted into the body.

The medical devices of the present invention include implantable and insertable medical devices that are used for systemic treatment and those that are used for the localized treatment of any mammalian tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, lungs, trachea, esophagus, intestines, stomach, brain, liver and pancreas, skeletal muscle, smooth muscle, breast, dermal tissue, cartilage, tooth and bone.

As used herein, "treatment" refers to the prevention of a disease or condition, the reduction or elimination of symptoms associated with a disease or condition, or the substantial or complete elimination of a disease or condition. Preferred subjects (also referred to as "patients") are vertebrate subjects, more preferably mammalian subjects and more preferably human subjects.

Specific examples of medical devices for use in conjunction with the present invention include both intravascular and intervascular medical devices, for example, vascular stents that deliver therapeutic agent into the vasculature for the treatment of restenosis. In these embodiments, the therapeutic agent is typically provided within a carrier layer or beneath a barrier layer or both.

As used herein, "polymers" are molecules containing one or more chains, each containing multiple copies of one or more constitutional units. An example of a common polymer is polystyrene

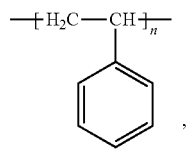

where n is an integer, typically an integer of 10 or more, more typically on the order of 10's, 100's, 1000's or even more, in which the chain contains styrene monomers:

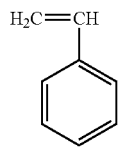

(i.e., the chain originates from, or has the appearance of originating from, the polymerization of styrene monomers, in this case, the addition polymerization of styrene monomers). As used herein, "copolymers" are polymers that contain at least two dissimilar constitutional units.

As used herein, a polymer "block" is a grouping of 10 or more constitutional units, commonly 20 or more, 50 or more, 100 or more, 200 or more, 500 or more, or even 1000 or more units. Blocks can be branched or unbranched. Blocks can contain a single type of constitutional unit (sometimes referred to herein as "homopolymeric blocks") or multiple types of constitutional units (sometimes referred to herein as "copolymeric blocks"). A "chain" is a linear (unbranched) grouping of 10 or more constitutional units (i.e., a linear block). Blocks can correspond to an entire polymer (e.g., a homopolymer, or a random, statistical, gradient, or periodic copolymer, for instance, an alternating copolymer.) Blocks can also correspond to portions of a block copolymer, which blocks can be formed, for example, from a single monomer, from two or more copolymers in a periodic, random, statistical or gradient distribution, and so forth.

Polymers for use in the phase separated polymeric regions of the invention can take on a number of configurations, which may be selected, for example, from cyclic, linear and branched configurations. Branched configurations include star-shaped configurations (e.g., configurations in which three or more chains emanate from a single branch point), comb configurations (e.g., configurations having a main chain and a plurality of side chains), dendritic configurations (e.g., arborescent and hyperbranched polymers), and so forth.

In some embodiments of the invention, the separated stable and disintegrable polymeric phases of the polymeric regions are provided by including a single polymer in the polymeric region.

For example, one or more stable polymeric phases and one or more disintegrable polymeric phases can be provided in the polymeric region by including a block copolymer that contains at least one stable block and at least one disintegrable block, which are phase separated from one another (i.e., they are immiscible). The stable and disintegrable blocks of the block copolymer may be present, for instance, as homopolymeric blocks (e.g., a repeating series of constitutional units of a single type) or as copolymeric blocks (e.g., constitutional units of two or more types, for instance, arranged in a periodic, random, statistical or gradient distribution). The block copolymer may be provided in a variety of configurations, including cyclic, linear and branched configurations. The at least one stable block (or the at least one disintegrable block) may be present in the copolymer, for example, as an endblock (e.g., as an endblock of a diblock copolymer), as a plurality of endblocks (e.g., as endblocks for a triblock copolymer or a star copolymer), as a midblock (e.g., as a midblock for a triblock copolymer or a star copolymer), as a main chain (e.g., as a main chain within a comb-shaped copolymer), as a side chain (e.g., as a side chain within a comb-shaped copolymer), and so forth.

In other embodiments, the separated stable and disintegrable polymeric phases of the polymeric regions of the present invention are provided by including two or more polymers in the polymeric region. The polymers may be, for example, homopolymers or copolymers (e.g., periodic, random, statistical, gradient, and block copolymers) and may be provided in a variety of configurations such as those described above. In these embodiments, the stable and disintegrable polymeric phases may each contain, independently, an entire polymer (e.g., a homopolymer, or a periodic or random copolymer), a portion of a polymer (e.g., a block of a block copolymer), an entire polymer and a portion of a polymer, two entire polymers, two portions of two polymers, and so forth.

Each of the stable and disintegrable phases of the phase separated polymeric regions of the invention may, independently, contain polymer blocks of the same monomeric composition, or they can contain polymer blocks that are of different monomeric composition so long as they are miscible with one another.

Again, such stable and disintegrable phases can be provided from a variety of sources, for example, from the following: a single copolymer (e.g., a block copolymer); multiple copolymers (e.g., periodic, random, statistical, gradient and/or block copolymers); multiple homopolymers; a single homopolymer and a single copolymer (e.g., a periodic, random, statistical, gradient or block copolymer), a single copolymer (e.g., a periodic, random, statistical, gradient or block copolymer) and multiple homopolymers; a single homopolymer and multiple copolymers (e.g., periodic, random, statistical, gradient and/or block copolymers); and so forth.

As one specific example, a polymeric region can be provided in accordance with the present invention, which has a stable polymeric phase that corresponds to a stable homopolymer or to a stable copolymer that does not phase separate from itself (e.g., a non-block copolymer, such as a random copolymer or a periodic copolymer, for instance, an alternating copolymer) and a disintegrable polymeric phase that corresponds to a disintegrable homopolymer or a disintegrable copolymer that does not phase separate from itself (e.g., a non-block copolymer).

As another specific example, two or more separate stable polymeric phases of different composition may be provided in the polymeric region, for example, by including a stable polymer that phase separates from itself internally (e.g., a block copolymer that contains two stable, phase-separated blocks), or by including two stable immiscible polymers (e.g., two stable homopolymers, two stable non-block copolymers, a stable homopolymer and a stable non-block copolymer, etc.).

Similarly, two or more separate disintegrable polymeric phases can be provided in the polymeric region, for example, by including two immiscible disintegrable polymers (e.g., two disintegrable homopolymers, two disintegrable non-block copolymers, or a disintegrable homopolymer and a disintegrable non-block copolymer), or they can also be provided by including a polymer that phase separates from itself internally (e.g., a block copolymer that contains two phase-separated, disintegrable blocks).

It should be clear at this point that the separated stable and disintegrable polymeric phases can be provided using a wide variety of polymers.

Some specific examples include homopolymers and copolymers (e.g., random, statistical, gradient, periodic and block copolymers) that consist of or contain one or more of the following biodisintegrable polymer blocks: (a) biodisintegrable blocks containing one or more biodisintegrable polyesters, including homopolymer and copolymer blocks containing one or more monomers selected from the following: hydroxyacids and lactones, such as glycolic acid, lactic acid, tartronic acid, fumaric acid, hydroxybutyric acid, hydroxyvaleric acid, dioxanone, caprolactone and valerolactone, (b) biodisintegrable blocks containing one or more biodisintegrable polyanhydrides, including homopolymer and copolymer blocks containing one or more diacids such as sebacic acid and 1,6-bis(p-carboxyphoxy) alkanes, for instance, 1,6-bis(p-carboxyphoxy) hexane and 1,6-bis(p-carboxyphoxy) propane; (c) biodisintegrable blocks containing one or more tyrosine-derived polycarbonates or polyester-amides, and (d) biodisintegrable blocks containing one or more polyorthoesters, among others.

Some particularly beneficial examples of homopolymers and copolymers include those that consist of or contain one or more biodegradable homopolymer or copolymer blocks that comprise one or more of the following monomers: glycolic acid, lactic acid, caprolactone, trimethylene carbonate, P-dioxanone, hydroxybutyrate, and hydroxyvalerate. Further examples of homopolymer or copolymer blocks include desaminotyrosine polyarylate blocks (tyrosine based polyarylates are available from TyRx Pharma, Inc., New Brunswick, N.J., USA and Reva Medical, Inc., San Diego, Calif., USA), desaminotryrosine polycarbonate blocks (available from Integra LifeSciences, Plainfield, N.J., USA), polyanhydride blocks such as those formed from therapeutic-based monomers (polyanhydrides are available from Polymerix Inc., Piscataway, N.J., USA), PEG-polybutyl terephthalate (available from SurModics, Inc., Eden Prairie, Minn., USA, IsoTis Orthobiolics, Inc., Irvine, Calif., USA), polyesteramides (available from MediVas LLC, California, USA), and biodegradable polyurethanes such as poly(ester urethanes).

Additional specific examples include water soluble homopolymers and copolymers (e.g., random, statistical, gradient, periodic and block copolymer blocks) that consist of or contain homopolymer or copolymer blocks selected from the following: alkylcelluloses such as methylcellulose, hydroxyalkylcelluloses such as hydroxymethylcellulose, hydroxyethylcellulose, hydroxypropylcellulose and hydroxybutylcellulose; hydroxyalkyl alkylcelluloses such as hydroxyethyl methylcellulose and hydroxypropyl methylcellulose; carboxyalkylcelluloses such as carboxymethylcellulose; alkali metal salts of carboxyalkylcelluloses such as sodium carboxymethylcellulose; carboxyalkylalkylcelluloses such as carboxymethylethylcellulose; carboxyalkylcellulose esters; starches; pectins such as sodium carboxymethylamylopectin; chitin derivatives such as chitosan; polysaccharides such as alginic acid, and alkali metal and ammonium salts thereof, carrageenans, galactomannans, traganth, agar-agar, gum arabicum, guar gum and xanthan gum; polyacrylic acids and salts thereof; polymethacrylic acids and salts thereof; polyvinylpyrrolidone, 1-vinyl-2-pyrrolidone, copolymers of polyvinylpyrrolidone with vinyl acetate; polyalkylene oxides such as polyethylene oxide and polypropylene oxide and copolymers of ethylene oxide and propylene oxide; polymers and copolymers of acrylamide and N,N dimethylacrylamide, polymers and copolymers of vinyl alcohol, polymers and copolymers of methyl vinyl ether, and so forth.

As indicated above, where block copolymers are provided that contain one or more dissolvable polymer blocks and one or more biostable hydrophobic polymer blocks are provided in a blend with another biostable polymer, if the hydrophobic biostable blocks are small relative to the dissolvable blocks, then the block copolymer may dissolve in vivo thereby forming pores, whereas if the biostable blocks are large relative to the dissolvable blocks (and the dissolvable blocks do not degrade), then the copolymer may not dissolve in vivo and no pores will form, although the release characteristics of a polymeric region containing such copolymers is typically affected.

In accordance with certain additional aspects of the present invention, polymeric regions are provided with one or more radiation disintegrable polymeric phases, which can be provided using a variety of polymers. Some specific examples include homopolymers and copolymers that consist of or contain one or more of the following radiation disintegrable polymer blocks: polytetrafluoroethylene, fluorinated ethylene polymer blocks, polyacetals, poly(methyl pentene), poly(methyl methacrylate), poly(vinyl chloride/vinyl acetate), collagen, cellulose, cellulose acetate, nylon 6, nylon 12, polypropylene, poly(2-methyl butene), poly(2-methyl pentene), polyisobutylene, and other polymeric blocks having alternating quaternary and secondary carbons, e.g., $(-CH_2-CR_1R_2-)_n$, where n is an integer, and $R_1$ and $R_2$ are organic radicals, for example, $C_1$-$C_{10}$ alkyl (which, as used herein, can be liner or branched, substituted or unsubstituted), $C_2$-$C_{20}$ alkoxyalkyl, $C_3$-$C_{20}$ alkylcarboxylic ester, and so forth.

On the other hand, the one or more biostable polymeric phases found in the polymeric regions of the present invention can also be provided using a variety of polymers, including a wide range of homopolymers and copolymers (e.g., random, statistical, gradient, periodic and block copolymers) having a range of configurations. Some specific examples of biostable homopolymers and copolymers can be selected from the following: polyolefins such as polyethylenes, polypropylenes, and polybutylenes, polyolefin copolymers, e.g., ethylenic copolymers such as ethylene vinyl acetate (EVA) copolymers, ethylene-methacrylic acid copolymers and ethylene-acrylic acid copolymers where some of the acid groups can be neutralized, e.g., with zinc or sodium ions (commonly known as ionomers); vinyl aromatic polymers such as polystyrene; vinyl aromatic copolymers such as styrene-ethylene-butylene copolymers (e.g., a polystyrene-polyethylene/butylene-polystyrene (SEBS) copolymer, available as Kraton® G series polymers), styrene-isobutylene copolymers (e.g., polystyrene-polyisobutylene-polystyrene (SIBS) copolymers such as those disclosed in U.S. Pat. No. 6,545,097 to Pinchuk), butadiene-styrene copolymers, and styrene-maleic acid (SMA) copolymers (e.g., random copolymers of styrene and maleic anhydride, such as those available from Nova Chemical, and alternating copolymers of styrene and maleic anhydride, such as those available from Scientific Polymer Products, Inc.); polyacetals; chloropolymers such as polyvinyl chloride (PVC); fluoropolymers such as polytetrafluoroethylene (PTFE); polyesters such as polyethyleneterephthalate (PET); polyester-ethers; polyamides such as nylon 6 and nylon 6,6; polyether; polyamide ethers such as polyether block amides (PEBA); silicones; polycarbonates; polyoctenamers; thermoplastic polyurethanes (TPU); and elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Carbothane®, Tecoflex®, Tecothane®, Tecophilic®, Tecoplast®, Pellethane®, Chronothane® and Chronoflex®).

Examples of biostable homopolymers and copolymers (e.g., biostable random, statistical, gradient, periodic and block copolymers) for the practice of the present invention include those that consist of or contain one or more biostable low and/or high $T_g$ homopolymer and/or copolymer blocks. A "low $T_g$ polymer block" is a polymer block that displays one or more glass transition temperatures ($T_g$), as measured by any of a number of techniques including differential scanning calorimetry (DSC), dynamic mechanical analysis (DMA), or dielectric analysis (DEA), that is below ambient temperature, typically below 25° C., below 0° C., below −25° C., or even below −50° C. Elevated or high $T_g$ polymer blocks are those that display at least one glass transition temperature that is above ambient temperature, more typically above 50° C., above 75° C., or even above 100° C. "Ambient temperature" is typically 25° C.-45° C., more typically body temperature (e.g., 35° C.-40° C.). As a result of their low glass transition temperatures, low $T_g$ polymer blocks are typically elastomeric at ambient temperature, whereas high $T_g$ polymer blocks are typically hard. (Homopolymers of some low $T_g$ polymer blocks, such as linear or branched silicone (e.g. polydimethylsiloxane), however, are viscous liquids or millable gums at room temperature and become elastomeric upon covalent cross-linking.)

Specific examples of biostable homopolymers and copolymers include those that consist of or contain one or more biostable low $T_g$ homopolymer or copolymer blocks, which in turn contain one or more monomers selected from the following (listed along with published $T_g$'s for homopolymers of the same): (1) acrylic monomers including: (a) alkyl acrylates such as methyl acrylate ($T_g$ 10° C.), ethyl acrylate ($T_g$ −24° C.), propyl acrylate, isopropyl acrylate ($T_g$ −11° C., isotactic), butyl acrylate ($T_g$ −54° C.), sec-butyl acrylate ($T_g$ −26° C.), isobutyl acrylate ($T_g$ −24° C.), cyclohexyl acrylate ($T_g$ 19° C.), 2-ethylhexyl acrylate ($T_g$ −50° C.), dodecyl acrylate ($T_g$ −3° C.) and hexadecyl acrylate ($T_g$ 35° C.), (b) arylalkyl acrylates such as benzyl acrylate ($T_g$ 6° C.), (c) alkoxy-alkyl acrylates such as 2-ethoxyethyl acrylate ($T_g$ −50° C.) and 2-methoxyethyl acrylate ($T_g$ −50° C.), (d) halo-alkyl acrylates such as 2,2,2-trifluoroethyl acrylate ($T_g$ −10° C.) and (e) cyano-alkyl acrylates such as 2-cyanoethyl acrylate ($T_g$ 4° C.); (2) methacrylic monomers including (a) alkyl methacrylates such as butyl methacrylate ($T_g$ 20° C.), hexyl methacrylate ($T_g$ −5° C.), 2-ethylhexyl methacrylate ($T_g$ −10° C.), octyl methacrylate ($T_g$ −20° C.), dodecyl methacrylate ($T_g$ −65° C.), hexadecyl methacrylate ($T_g$ 15° C.) and octadecyl methacrylate ($T_g$ −100° C.) and (b) aminoalkyl methacrylates such as diethylaminoethyl methacrylate ($T_g$ 20° C.) and 2-tert-butyl-aminoethyl methacrylate ($T_g$ 33° C.); (3) vinyl ether monomers including (a) alkyl vinyl ethers such as ethyl vinyl ether ($T_g$ −43° C.), propyl vinyl ether ($T_g$ −49° C.), butyl vinyl ether ($T_g$ −55° C.), isobutyl vinyl ether ($T_g$ −19° C.), 2-ethylhexyl vinyl ether ($T_g$ −66° C.) and dodecyl vinyl ether ($T_g$ −62° C.); (4) cyclic ether monomers include tetrahydrofuran ($T_g$ −84° C.), trimethylene oxide ($T_g$ −78° C.), ethylene oxide ($T_g$ −66° C.), propylene oxide ($T_g$ −75° C.), methyl glycidyl ether ($T_g$ −62° C.), butyl glycidyl ether ($T_g$ −79° C.), allyl glycidyl ether ($T_g$ −78° C.), epibromohydrin ($T_g$ −14° C.), epichlorohydrin ($T_g$ −22° C.), 1,2-epoxybutane ($T_g$ −70° C.), 1,2-epoxyoctane ($T_g$ −67° C.) and 1,2-epoxydecane ($T_g$ −70° C.); (5) ester monomers (other than acrylates and methacrylates) including ethylene malonate ($T_g$ −29° C.), vinyl acetate ($T_g$ 30° C.), and vinyl propionate ($T_g$ 10° C.); (6) alkene monomers including ethylene, propylene ($T_g$ −8 to −13° C.), isobutylene ($T_g$ −73° C.), 1-butene ($T_g$ −24° C.), trans-butadiene ($T_g$ −58° C.), 4-methyl pentene ($T_g$ 29° C.), 1-octene ($T_g$ −63° C.) and other α-olefins, cis-isoprene ($T_g$ −63° C.), and trans-isoprene ($T_g$ −66° C.); (7) halogenated alkene monomers including vinylidene chloride ($T_g$ −18° C.), vinylidene fluoride ($T_g$ −40° C.), cis-chlorobutadiene ($T_g$ −20° C.), and trans-chlorobutadiene ($T_g$ −40° C.); and (8) siloxane monomers including dimethylsiloxane ($T_g$ −127° C.), diethylsiloxane, methylethylsiloxane, methylphenylsiloxane ($T_g$ −86° C.), and diphenylsiloxane.

Specific examples of biostable homopolymers and copolymers further include those that consist of or contain one or more biostable high $T_g$ homopolymer or copolymer blocks, which in turn contain one or more monomers selected from the following: (1) vinyl aromatic monomers including (a) unsubstituted vinyl aromatics, such as atactic styrene ($T_g$ 100° C.), isotactic styrene ($T_g$ 100° C.) and 2-vinyl naphthalene ($T_g$ 151° C.), (b) vinyl substituted aromatics such as α-methyl styrene, and (c) ring-substituted vinyl aromatics including ring-alkylated vinyl aromatics such as 3-methylstyrene ($T_g$ 97° C.), 4-methylstyrene ($T_g$ 97° C.), 2,4-dimethylstyrene ($T_g$ 112° C.), 2,5-dimethylstyrene ($T_g$ 143° C.), 3,5-dimethylstyrene ($T_g$ 104° C.), 2,4,6-trimethylstyrene ($T_g$ 162° C.), and 4-tert-butylstyrene ($T_g$ 127° C.), ring-alkoxylated vinyl aromatics, such as 4-methoxystyrene ($T_g$ 113° C.) and 4-ethoxystyrene ($T_g$ 86° C.), ring-halogenated vinyl aromatics such as 2-chlorostyrene ($T_g$ 119° C.), 3-chlorostyrene ($T_g$ 90° C.), 4-chlorostyrene ($T_g$ 110° C.), 2,6-dichlorostyrene ($T_g$ 167° C.), 4-bromostyrene ($Tg_g$ 118° C.) and 4-fluorostyrene ($T_g$ 95° C.) and ring-ester-substituted vinyl aromatics such as 4-acetoxystyrene ($T_g$ 116° C.); (2) other vinyl monomers including (a) vinyl esters such as vinyl benzoate ($T_g$ 71° C.), vinyl 4-tert-butyl benzoate ($T_g$ 101° C.), vinyl cyclohexanoate ($T_g$ 76° C.), vinyl pivalate ($T_g$ 86° C.), vinyl trifluoroacetate ($T_g$ 46° C.), vinyl butyral ($T_g$ 49° C.), (b) vinyl amines such as 2-vinyl pyridine ($T_g$ 104° C.), 4-vinyl pyridine ($T_g$ 142° C.), and vinyl carbazole ($T_g$ 227° C.), (c) vinyl halides such as vinyl chloride ($T_g$ 81° C.) and vinyl fluoride ($T_g$ 40° C.); (d) alkyl vinyl ethers such as tert-butyl vinyl ether ($T_g$ 88° C.) and cyclohexyl vinyl ether ($T_g$ 81° C.), and (e) other vinyl compounds such as vinyl ferrocene ($T_g$ 189° C.); (3) other aromatic monomers including acenaphthalene ($T_g$ 214° C.) and indene ($T_g$ 85° C.); (4) methacrylic monomers including (a) methacrylic acid anhydride ($T_g$ 159° C.), (b) methacrylic acid esters (methacrylates) including (i) alkyl methacrylates such as atactic methyl methacrylate ($T_g$ 105-120° C.), syndiotactic methyl methacrylate ($T_g$ 115° C.), ethyl methacrylate ($T_g$ 65° C.), isopropyl methacrylate ($T_g$ 81° C.), isobutyl methacrylate ($T_g$ 53° C.), t-butyl methacrylate ($T_g$ 118° C.) and cyclohexyl methacrylate ($T_g$ 92° C.), (ii) aromatic methacrylates such as phenyl methacrylate ($T_g$ 110° C.) and including aromatic alkyl methacrylates such as benzyl methacrylate ($T_g$ 54° C.), (iii) hydroxyalkyl methacrylates such as 2-hydroxyethyl methacrylate ($T_g$ 57° C.) and 2-hydroxypropyl methacrylate ($T_g$ 76° C.), (iv) additional methacrylates including isobornyl methacrylate ($T_g$ 110° C.) and trimethylsilyl methacrylate ($T_g$ 68° C.), and (c) other methacrylic-acid derivatives including methacrylonitrile ($T_g$ 120° C.); (5) acrylic monomers including (a) certain acrylic acid esters such as tert-butyl acrylate ($T_g$ 43-107° C.), hexyl acrylate ($T_g$ 57° C.) and isobornyl acrylate ($T_g$ 94° C.); and (b) other acrylic-acid derivatives including acrylonitrile ($T_g$ 125° C.).

In accordance with certain aspects, the polymeric regions of the present invention are provided with one or more radiation stable polymeric phases, which can be provided using a variety of polymers. Some specific examples include homopolymers and copolymers that consist of or contain one or more radiation stable homopolymer or copolymer blocks, which can contain one or more aromatic and/or acrylic monomers selected from the following: vinyl aromatic monomers such as those listed above, including unsubstituted vinyl aromatic monomers, vinyl substituted aromatic monomers, and ring-substituted vinyl aromatic monomers such as ring-alkylated vinyl aromatic monomers, ring-alkoxylated vinyl aromatic monomers, ring-halogenated vinyl aromatic monomers and ring-ester-substituted vinyl aromatics; and other aromatic monomers beyond vinyl aromatic monomers such as those listed above, including aromatic methacrylates, aromatic acrylates, alkyl phenylsiloxane, diphenylsiloxane, acenaphthalene and indene, acrylic monomers such as those listed above, including acrylic acid esters such as alkyl acrylates, arylalkyl acrylates, alkoxyalkyl acrylates, halo-alkyl acrylates, cyano-alkyl acrylates, and other acrylic-acid derivatives such as acrylonitrile, among others. Polystyrene and poly(vinyl acrylate) and poly(isobornyl acrylate) are specific examples of beneficial radiation stable blocks.

Based on the above and other criteria, various combinations of stable and disintegrable homopolymer and copolymer blocks can be provided using various homopolymers and copolymers to create a wide range of phase separated polymeric region in accordance with the present invention.

According to one specific example, a phase separated polymeric region is provided which contains the following: (a) a biostable vinyl aromatic copolymer such as a styrene-ethylene-butylene copolymer (e.g., SEBS), a styrene-isobutylene copolymer (e.g., SIBS), a butadiene-styrene copolymer, or a styrene-maleic acid copolymer with (b) a biodisintegrable polyester such as a polycaprolactone, polylactide, polyglycolide, or poly(lactide-co-glycolide). Upon removal of the biodegradable polyester, a porous polymeric region consisting of the vinyl aromatic copolymer remains. Vinyl aromatic copolymers, such as polystyrene-polyisobutylene-polystyrene triblock copolymers, are known to have exceptional biostability and biocompatibility.

Thus, in some embodiments, block copolymers are included in the polymeric regions of the invention, which block copolymers can provide the following: (a) blocks corresponding to two or more stable phases, (b) blocks corresponding to two or more disintegrable phases, or (c) blocks corresponding to at least one stable phase and at least one disintegrable phase.

Block copolymers can be provided in a wide variety of configurations. A few examples are set forth below for copolymers that contain two phase separatable blocks, "A" and "B," both of which can be stable, both of which can be disintegrable, or one of which can be stable and the other of which can be disintegrable. These blocks can be homopolymer blocks or copolymer blocks (for instance, copolymer blocks containing random or periodically repeating constitutional units, a specific example of which is the central ethylene-butylene block found within SEBS triblock copolymers such as Kraton® copolymers). These blocks can be selected, for example, from various stable and disintegrable blocks such as those set forth above. Examples include block copolymers having the following structures: (a) $AB_n$ or $BA_n$, where n is an integer, for example, AB (diblock), BAB or ABA (triblock copolymers), $AB_3$ or $BA_3$ (three-arm, star-shaped copolymers), etc. Other examples include alternating configurations such as $B(AB)_n$ or $A(BA)_n$. Note that it is common to disregard the presence of small entities such as the seed molecules X in describing block copolymers, for example, with $X-(AB)_n$ and $X-(BA)_n$ being designated $AB_n$ and $BA_n$, respectively.

A specific example is a copolymer, $AB_n$, where A is a low $T_g$ biostable elastomeric block, for example, a homopolymeric or copolymeric polyolefin block such as polyisobutylene or poly(ethylene-co-butylene), and B is a biodisintegrable block, for example, a homopolymeric or copolymeric poly(alpha-hydroxy acid) block such polycaprolactone, polylactide, polyglycolide, or poly(lactide-co-glycolide), or vice versa (i.e., where A is the low $T_g$ biostable elastomeric block, while B is the biodisintegrable block). Such polymers include diblock copolymers (where n=1), triblock copolymers (where n=2) and star copolymers (where n=3 or more).

Another example is a copolymer containing a low $T_g$ biostable elastomeric main chain and numerous biodisintegrable polymer sidechains (i.e., a comb copolymer), or vice versa.

Polymers such as those described herein can be formed by a number of procedures that are known in the polymer art.

For instance, in accordance with one example, copolymers can be synthesized by copolymerizing a low $T_g$ polymer block such as a polyisobutylene block with monomers that are capable of forming biodisintegrable polymer segments (e.g., biodisintegrable endblocks), or vice versa. For example, a diblock copolymer of polyisobutylene-polycaprolactone and a triblock copolymer of polycaprolactone-polyisobutylene-polycaprolactone can be synthesized through the combination of a cationic living polymerization of isobutylene and the ring-opening polymerization of caprolactone. A polyisobutylene macroinitiator, for instance, can be prepared which contains one or more initiation sites (e.g., hydroxyl end-functional polyisobutylene) from which ring-opening polymerization of biodisintegrable endblocks can occur to create a multiblock polymer. Hence, when the biodisintegrable materials comprise cyclic esters such as lactide, caprolactone, cyclic carbonate, or glycolide, polyisobutylene macroinitiators can be used to initiate the ring opening polymerization of the cyclic esters, thereby forming a variety of copolymers.

As another example, a copolymer is formed by reacting a di-hydroxy-terminated polyolefin with 2-bromo-isobutyrl bromide to form an α-bromoester initiating group at each end of the polyolefin molecule. The difunctional macro-initiator can then be used to form an endblock graft copolymer by living free-radical copolymerization of a biodisintegrable macromonomer (e.g., polylactide) with another mono-unsaturated monomer, for example, styrene or methyl methacrylate.

As yet another example, a pentablock copolymer of the formula B-C-A-C-B is synthesized, where A, B or C is a biodistintegrable block. In a specific example, B is a biodisintegrable block, for example, a homopolymeric or copolymeric poly(alpha-hydroxy acid) block such a polylactide, polyglycolide, or poly(lactide-co-glycolide) block, and A and C are biostable blocks, for example, A can be a biostable low $T_g$ elastomeric block, for example, a homopolymeric or copolymeric polyolefin block such as a polyisobutylene or poly(ethylene-co-butylene), and C can be biostable hard, high $T_g$ block, for example, a poly(vinyl aromatic) block such as polystyrene. Upon removal of the biodegradable blocks, the block copolymer C-A-C remains, one of example of which is polystyrene-polyisobutylene-polystyrene (SIBS), which is known to be mechanically strong, biostable and biocompatible. Such pentablock copolymers can be formed using various techniques, including monomer addition, for example, where a biodisintegrable monomer is polymerized onto a A-B-A tri-block copolymer by a living polymerization reaction. Alternatively, preformed, mono-functional-terminated biodisintegrable blocks can be coupled to di-functionalized ABA triblock copolymers to form pentablock structures.

In addition to selecting polymers for the polymeric regions based on their relative stability/disintegrability, polymers can also be selected based on their relative hydrophilicity/hydrophobicity. Examples of monomers for forming relatively hydrophilic, biostable polymer blocks include ethylene oxide, hydroxyethylmethacrylate and 1-vinyl-2-pyrrolidinone, examples of monomers for forming of relatively hydrophobic biostable polymer blocks include styrene and methyl methacrylate, examples of monomers for forming relatively hydrophilic biodisintegrable polymer blocks include glycolic acid, and examples of monomers for forming relatively hydrophobic biodisintegrable polymer blocks include caprolactone. These monomers can be provided in the polymeric regions of the invention, either within homopolymers or within copolymers (e.g., in random, statistical, gradient, periodic or block copolymers), with the overall hydrophobicity/hydrophilicity of the polymer region depending, for example, upon the relative hydrophobicity/hydrophilicity of the monomers that are selected as well as the relative proportions of each monomer within the region.

The medical devices of the invention are provided with therapeutic agents in some embodiments, and without therapeutic agents in other embodiments. Even where a therapeutic agent is not included, the polymeric regions can nonetheless affect cell growth. For instance, the removal of disintegrable polymeric phase(s) of nanoscale dimensions, either in vivo upon device implantation or insertion, or ex vivo during device fabrication, will lead to nanoporous polymeric regions within the medical devices. To the extent that these nanopores are located at the surface, they will create nanostructured surfaces, which are highly sought after in tissue engineering applications. For example, as noted above, it is known that nanostructured surfaces can directly interact with cell receptors, thereby controlling the adhesion or non-adhesion of cells to the surface.

Where one or more therapeutic agents are included in the medical devices of the invention, they can be incorporated in a number of ways, for example, by including the therapeutic agent(s) within a carrier region, by including the therapeutic agent(s) beneath a barrier region, or both.

By "carrier region" is meant a polymeric region which further comprises a therapeutic agent and from which the therapeutic agent is released. For example, in some embodiments, a carrier region constitutes the entirety of the medical device. In other embodiments, a carrier region is provided which corresponds to only a portion of the device, for example, disposed over all or a portion of a medical device substrate in the form of a layer.

At least two distinct types of porous carrier regions are utilized in conjunction with the various embodiments of the present invention. In some embodiments, a porous polymeric region is formed from a phase separated polymeric region ex vivo. A therapeutic agent is then introduced into the porous structure and the device is subsequently introduced into a patient. In other embodiments, a therapeutic agent in provided within a phase separated polymeric region that contains at least one biostable polymeric phase and at least one biodisintegrable polymeric phase. With such devices, a porous polymeric region is created in vivo by the disintegration of the at least one biodisintegrable phase. This potentially creates additional avenues for escape of therapeutic agent from the region, and it is expected to increase the amount of therapeutic agent that is released (thereby reducing that amount of drug that ultimately remains in the carrier region, improving delivery efficiency). This is in contrast with polymeric carrier regions that are formed using only biostable polymers, in which case therapeutic agent can be trapped within the polymeric matrix, unable to be eluted from the device. Such a trapping issues are particularly acute for high molecular weight therapeutic agents such as polysaccharides, polypeptides (e.g., proteins) or polynucleotides (e.g., plasmid DNA). As used herein, a high molecular weight therapeutic agent is one having a molecular weight of greater than 5,000 and commonly greater than 10,000, 25,000, 50,000, 100,000, 250,000, 500,000, 1,000,000 or even more.

Thus certain aspects of the present invention are advantageous in that they provide a mechanism for increasing the rate and/or cumulative amount of therapeutic agent that is released.

By "barrier region" is meant a region, which is disposed between a source of therapeutic agent and a site of intended release, and which controls the rate at which therapeutic agent is released. In some embodiments, the medical devices of the present invention include a barrier region that surrounds a source of therapeutic agent. In other embodiments, the barrier region is disposed, for example, in the form of a layer, over a source of therapeutic agent, which is in turn disposed over all or a portion of a medical device substrate.

At least two distinct types of porous barrier regions are utilized in conjunction with the present invention. In some embodiments, a porous polymeric region is formed from a phase separated polymeric region ex vivo, and disposed over a source of therapeutic agent, before introducing the device into a patient. In other embodiments, a therapeutic agent in provided beneath a phase separated polymeric region that contains at least one biostable polymeric phase and at least one biodisintegrable polymeric phase. A porous polymeric region is then created by the disintegration of the at least one biodisintegrable phase in vivo upon introducing the device into a patient.

Thus, in some embodiments where a polymeric region in accordance with the present invention is used as a barrier region, the disintegration of the at least one disintegrable phase within the polymeric region, either in vivo or ex vivo, results in the formation a porous drug release membrane, which regulates transport of the therapeutic agent to the patient. Transport is enhanced in embodiments where the stable and disintegrable phase(s) are co-continuous and extend throughout the thickness of the polymeric region. See, for example, configuration "e" of FIG. 1, which will produce interconnected nanopores that extend through the polymeric region. Of course many other polymeric phase configurations are possible.

As indicated previously, where block copolymers that contain one or more dissolvable polymer blocks and one or more hydrophobic biostable polymer blocks are blended with at least one other biostable polymer, if the biostable blocks are large relative to the dissolvable blocks (and the dissolvable blocks do not degrade), then the copolymer may not dissolve in vivo and no pores will form. However, the release characteristics of polymeric regions containing such copolymers are commonly enhanced, whether such polymeric regions are employed as carrier regions or as barrier regions.

A wide range of therapeutic agent loadings can be used in connection with the medical devices of the present invention, with the therapeutically effective amount being readily determined by those of ordinary skill in the art and ultimately depending, for example, upon the condition to be treated, the age, sex and condition of the patient, the nature of the therapeutic agent, the nature of the polymeric region(s), the nature of the medical device, and so forth.

The release profiles associated with the polymeric regions of the present invention can be modified in a number of ways, including changing the composition and molecular weight of the polymer blocks that form the biostable polymer phases and, where the disintegrable polymer phases are introduced into the subject (e.g., where the disintegrable polymer phases are not removed ex vivo), changing the composition and molecular weight of the polymer blocks that form the biodisintegrable polymer phases, as well as changing the relative volumes of the biostable and biodisintegrable phases. For example, as discussed above in conjunction with FIG. 1, the morphology of the disintegrable and stable phases, will typically vary with the relative amounts of disintegrable and stable polymer blocks in the composition.

As another example, the degradation rate of certain polymer blocks forming biodisintegrable polymer phases, and hence the rate at which nanopores are formed in vivo, will vary depending on the nature of the biodisintegrable polymer blocks selected (e.g., the monomeric constituents, molecular weight and crystallinity of the biodisintegrable polymer blocks) and on the size and morphology of the biodisintegrable polymeric phases that are occupied by the biodisintegrable polymer blocks. The rate of degradation within a patient may vary, for example, from a few hours to several months. Obviously, the use a rapidly disintegrable polymer will shorten the time required to develop a porous structure, whereas a slowly disintegrable polymer will lengthen the time.

In the specific instance where a block copolymer is employed, which has both biostable and biodisintegrable blocks, the release profile can be modified by changing composition and/or length (molecular weight) of the biostable and/or biodisintegrable blocks, by changing the configuration of the copolymer (e.g., linear copolymer vs. star shaped copolymer vs. comb copolymer) and/or by changing the position of the biostable and/or biodisintegrable blocks within the copolymer (e.g., midblock as opposed to endblock, main chain as opposed to side chain, etc.).

Where a therapeutic agent is provided within a phase separated carrier region that contains at least one biostable polymeric phase and at least one biodisintegrable polymeric phase, the therapeutic agent may be concentrated, for example: (a) within the biodisintegrable polymeric phase, (b) within the biostable polymeric phase, (c) at the interfaces between the biostable and biodisintegrable phases, and so forth. This partitioning may be adjusted, for example, by varying the hydrophilicity/hydrophobicity of the various phases as discussed above. For instance, in some embodiments, the concentration of therapeutic agent in the biodisintegrable polymeric phases is increased by closely matching the hydrophilicity/hydrophobicity of the therapeutic agent with that of the polymer blocks that form the biodisintegrable polymeric phases. Analogously, in some embodiments, the concentration of therapeutic agent in the biostable polymeric phases is increased by closely matching the hydrophilicity/hydrophobicity of the therapeutic agent with that of the polymer blocks that form the biostable polymeric phases. Where the hydrophilicity/hydrophobicity of the therapeutic agent differs substantially from the hydrophilicity/hydrophobicity of both the stable and disintegrable phases, the therapeutic agent is expected to concentrate at the interfaces between the stable and disintegrable phases.

The release profile associated with the polymeric regions of the medical device of the invention can also be modified by changing the number, order, thickness, or position of carrier and barrier layers with respect to one another. For example, the release profile can be modified by varying the thickness of the carrier and barrier layers. Moreover, multiple polymeric regions can be employed to modify the release profile, for example, (a) a barrier layer in accordance with the present invention can be positioned over a carrier layer in accordance with the present invention, (b) multiple carrier layers of the invention, either of the same or different content (e.g., different polymer and/or therapeutic agent content) can be stacked on top of one another, either with or without intervening barrier layers, (c) multiple carrier layers of the invention of differing compositions can be positioned laterally to one another, and so forth.

Therapeutic agents may be used singly or in combination in the medical devices of the present invention. "Drugs," "therapeutic agents," "pharmaceutically active agents," "pharmaceutically active materials," and other related terms may be used interchangeably herein. These terms include genetic therapeutic agents, non-genetic therapeutic agents and cells.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin; (t) beta-blockers, (u) bARKct inhibitors, (v) phospholamban inhibitors, and (w) Serca 2 gene/protein.

Preferred non-genetic therapeutic agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel and Ridogrel.

Exemplary genetic therapeutic agents for use in connection with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor $\alpha$ and $\beta$, platelet-derived endothelial growth factor, platelet-derived growth factor, tumor necrosis factor $\alpha$, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including $\alpha$-antagonists such as prazosin and bunazosine, $\beta$-antagonists such as propranolol and $\alpha/\beta$-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and $\beta$-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

Numerous techniques are available for forming phase separated polymeric regions in accordance with the present invention. For example, where the selected polymer or polymers has/have thermoplastic characteristics, a variety of standard thermoplastic processing techniques can be used to form the phase separated polymeric release regions, including compression molding, injection molding, blow molding, spinning, vacuum forming and calendaring, as well as extrusion into sheets, fibers, rods, tubes and other cross-sectional profiles of various lengths. Using these and other techniques, entire devices or portions thereof can be made. For example, an entire stent can be extruded using the above techniques. As another example, a coating can be provided by extruding a coating layer onto a pre-existing stent. As yet another example, a coating can be co-extruded along with an underlying stent body. If a therapeutic agent is stable at processing temperatures, then it can be combined with the copolymer prior to thermoplastic processing, producing a therapeutic-agent-containing carrier region. Alternatively, a therapeutic agent can be introduced subsequent to the formation of the phase separated polymeric region, or subsequent to the formation of the porous polymeric region ex vivo, using techniques discussed below, such as imbibing, etc.

Solvent-based techniques are generally preferred as techniques for forming the phase separated polymeric regions of the present invention. Using these techniques, phase separated polymeric regions can be formed by first providing a solution that contains the polymer or polymers that will ultimately form the phase separated polymeric regions (as well as dissolved or dispersed therapeutic agents and/or other optional agents, in some embodiments), followed by removal of the solvent, which leads to phase separation. It is well known in the polymer art that block copolymers can readily phase separate into phase domains on the order of tens of nanometers across.

The morphology of the phases that are produced, including the size, shape, orientation and connectivity of the phases, depends upon a number of factors, including the relative amounts of the biodisintegrable and biostable blocks within the solution, the composition and molecular weight of the biodisintegrable and biostable polymer blocks, the particular solvent species that form the solvent, the concentration of the polymer(s) in the solution, the temperature at which the solvent evaporation proceeds, the rate of evaporation of the solvent (e.g., dictated by solvent volatility, spraying pressure, and flow rate for a spraying process), and so forth. In addition, the phases can be oriented using electric fields, magnetic fields, zone casting, or other methods known in the polymer field.

As a general rule of thumb, conditions deviating significantly from equilibrium tend to enhance the production of co-continuous phases (which lead to an interconnected network of pores), while conditions approaching equilibrium conditions tend to produce more regular structures such as rods and lamina. When only a portion of such rod/lamina morphologies are removed, very interesting interconnected nanoporous-morphology are expected.

As indicated above, in a typical solvent based technique, a solution containing the polymer or polymers that will ultimately form the phase separated polymeric region (i.e., a "polymer solution") is formed. The solvent that is selected will contain one or more solvent species, which are generally selected based on their ability to dissolve the polymer or polymers that form the polymeric region as well as other factors, including drying rate, surface tension, etc. Generally several solvents will be tested to see which provides polymeric regions having the best characteristics.

Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

Where appropriate, such techniques can be repeated or combined to build up a polymeric layer to a desired thickness. The thickness of the polymeric layer can be varied in other ways as well. For example, in one preferred process, solvent spraying, coating thickness can be increased by modification of coating process parameters, including increasing spray flow rate, slowing the movement between the substrate to be coated and the spray nozzle, providing repeated passes and so forth. These parameters will also influence phase morphology.

In some embodiments, a polymer solution is applied to a substrate to form a polymeric region. For example, the substrate can correspond to all or a portion of an implantable or insertable medical device, such as a stent, to which a polymeric layer is applied. The substrate can also be, for example, a template, such as a mold, from which the polymeric region is removed after solvent elimination. In other embodiments, for example, fiber forming techniques, the polymeric region is formed without the aid of a substrate.

In certain embodiments, at least one therapeutic agent is added to the polymer solution, for example, in dissolved or dispersed form, and hence co-established with the phase separated polymeric region. In other embodiments, on the other hand, the therapeutic agent is dissolved or dispersed within a solvent, and the resulting solution contacted (e.g., using one or more of the application techniques described above, such as dipping, spraying, etc.) with a previously formed polymer region. The previously formed polymer region can be, for example, a phase separated polymeric region containing biostable and biodisintegrable polymeric phases, or it can be a porous polymeric region created by subjecting a phase separated polymeric region to ex vivo conditions whereby disintegrable polymeric phase(s) are selectively removed.

In contrast to carrier regions, barrier regions are formed over a therapeutic-agent-containing region. In some embodiments, a phase separated polymeric region, which contains at least one biostable polymeric phase and at least one biodisintegrable polymeric phase, is formed over a therapeutic-agent-containing region, for example, using one of the solvent based or thermoplastic techniques described above. In other embodiments, a previously formed polymeric region is applied over a therapeutic agent containing region. For example, a porous polymeric region may be created ex vivo as described in the prior paragraph and applied over a source of therapeutic agent.

Where the polymeric region is formed using a solvent-based technique, it is preferably dried after application to remove the solvent species. The polymeric region typically further conforms to any underlying surface during the drying process.

As indicated above, in some embodiments of the invention, porous polymeric regions are formed ex vivo by methods in which at least one disintegrable phase is selectively removed from at least one stable polymeric phase. Examples of conditions which can be used to selectively remove the at least one disintegrable polymeric phase include exposure to elevated temperatures, exposure to aqueous and/or organic solvents at temperatures and pressures that are effective to dissolve the disintegrable polymeric phases, exposure to reactive chemical species (including biological fluids) at concentrations, temperatures and pressures that result in the degradation of the at least one disintegrable polymeric phase (e.g., chemical lysis including hydrolysis, catalytic breakdown, etc.), exposure to radiation levels sufficient to cause chain scission within the at least one disintegrable polymeric phase, and so forth. The key to the success of each technique is ability to provide a phase separated region which contains at least one polymer phase that is stable under such conditions, and which contains at least one other polymer phase that is not stable under such conditions and thus can be removed.

For example, the phase separated polymeric region can be immersed at room or elevated temperature within a solvent (e.g., water, organic solvent, or a combination thereof) that acts as a good solvent for the disintegrable polymeric phase, but does not dissolve the stable polymer phase, which ultimately forms the porous polymeric region. One specific example of such a polymeric region is a phase separated blend of polystyrene-polyisobutylene-polystyrene (SIBS), a stable triblock copolymer, and polyethylene oxide (PEO). Because the PEO is water-soluble, it can be removed using water as a solvent. Where the polymer is dissolved, rather than broken down, the disintegrable polymeric phases generally correspond to homopolymers or copolymers which are distinct from the homopolymers or copolymers that form the stable polymer phases which are not removed. Otherwise, the disintegrable polymeric phases will not be readily separable from the stable polymeric phases (e.g., due to the presence of covalent bonds between the phases) and pores will not be formed. The same is true for other techniques besides dissolution that do not result in bond cleavage, including systems requiring melting or sublimation of disintegrable polymeric phases.

In another specific example, a polyisobutylene-polystyrene-polyisobutylene triblock copolymer is subjected to a dose of radiation that is effective to cause chain scission within the radiation sensitive polyisobutylene blocks, with little to no chain scission within the radiation stable polystyrene blocks.

Where the disintegrable phase is removed ex vivo, certain parts of the polymeric region can optionally be masked, resulting in the selective removal of the disintegrable phases in some areas (e.g., for the creation of nanoporous polymeric regions), whereas in other areas the disintegrable regions remain intact (e.g., to enhance mechanical integrity).

Once a porous polymeric region is produced ex vivo, in some embodiments, a therapeutic agent is introduced into the pores thereof, for example, by imbibing with a solution as discussed above, or by another process such as by gaseous diffusion, or by using a supercritical fluid to carry the therapeutic agent into the pores, and so forth.

In other aspects of the invention, a medical device containing a phase separated polymeric region, which contains at least one biostable polymeric phase and at least one biodisintegrable polymeric phase, is administered to a patient with its biodisintegrable polymeric phase intact. In embodiments where the biological milieu removes the disintegrable phase, a porous polymeric region is produced in vivo. In some instances, a therapeutic agent is also provided within or beneath the polymeric region, in which case the therapeutic agent commonly released upon administration to the patient.

The in vivo disintegration of the biodisintegrable polymer phase may proceed by a variety of mechanisms including dissolution (e.g., where the polymer is soluble) and/or chemical breakdown (wherein the polymer is at least partially biodegradable). Breakdown of the biodisintegrable phases commonly involves hydrolysis of the biodisintegrable polymer blocks that make up the biodisintegrable phases into biologically acceptable, progressively smaller compounds. For example, poly(lactic acid), poly(glycolic acid) and their copolymers eventually break down into lactic acid and glycolic acid, and enter the Kreb's cycle, whereby they are further broken down into carbon dioxide and water and excreted through normal processes.

Biodisintegration may take place in some embodiments, for example, through bulk hydrolysis, in which the polymer degrades in a fairly uniform manner throughout the polymer matrix. However, in other embodiments, for example, where biodisintegrable blocks comprise polyorthoesters or polyanhydrides, the disintegration typically occurs at the surface of the polymer, resulting in a release rate that is proportional to the surface area of the release region.

As noted above, therapeutic agents may be provided within or beneath phase separated polymeric regions that contain at least one biostable polymeric phase and at least one biodisintegrable polymeric phase, in which case the therapeutic agents may be released into the biological milieu. Although not wishing to be bound by theory, it is believed that the release of the therapeutic agent in these embodiments will occur by one or more of the following mechanisms, among others: by diffusion of the therapeutic agent within an intact polymeric phase, by swelling/hydration of a polymeric phase followed by diffusion of the therapeutic agent within the swelled/hydrated polymeric phase, and by polymer degradation.

With respect to polymer degradation, in embodiments where the therapeutic is preferentially located within the biodisintegrable phase(s) of the phase separated polymeric region (e.g., due to hydrophilic/hydrophobic effects as discussed above), degradation of the polymer is expected to release the therapeutic agent within the pores, thereby controlling the release rate of the therapeutic agent. On the other hand, in embodiments where the therapeutic is preferentially located within the biostable phase(s) of the phase separated polymeric region, the degradation of the polymer is expected to control the release of therapeutic agent by creating pores or channels, which can be filled by ambient fluids, into which the therapeutic agent can diffuse.

Similarly, in other embodiments where the therapeutic agent is provided beneath the phase separated polymeric region, degradation of the polymer assists in creating pores or channels which are expected to assist in controlling the release rate of the therapeutic. In other words, the degradation of the polymer creates a rate controlling, porous membrane.

Where the release rate of the therapeutic agent occurs primarily by diffusion through pores, the release rate may be controlled by the pore size and tortuosity of the porous matrix, as well as other physical and chemical characteristics of the porous polymeric region.

EXAMPLE 1

Synthesis and Characterization of Poly(caprolactone)-Polyisobutylene-Poly(caprolactone) Block Copolymer Block Copolymer Synthesis.

1. Synthesis of Hydroxyl End-Functional Polyisobutylene Macroinitiator

Polyisobutylene having a carboxylate end group is synthesized via a living cationic polymerization process. [Isobutylene]=0.09 M, [2,6-di-tert-butylpyridine (DTBP, Aldrich)]= $3 \times 10^{-3}$ M as a proton trap, and [2-chloro-2,4,4-trimethylpentane (TMPCl)]=$2 \times 10^{-3}$ M as an initiator in hexane/methyl chloride (MeCl) (60/40 v/v) are added to a prechilled 400 mL round flask. The polymerization of isobutylene is initiated by the addition of TiCl$_4$ stock solution ([TiCl$_4$]=$3.6 \times 10^{-2}$ M) at $-80°$ C. and is polymerized for 1 hour. The living polyisobutylene is capped in-situ by the addition of 2 equivalents of 1,1-diphenylethylene (DPE, Aldrich) or 1,1-p-ditolylethylene (DTE, Aldrich) stock solution to functionalize the polyisobutylene chain end. After 1 hour capping time, 2 equivalents of [(2-methyl-1-methoxy-1-trimethylsiloxy-propene (MTSP) stock solution is added to the reaction mixture. After 1 h reaction time, the reaction mixture is quenched with pre-chilled methanol and poured into NH$_4$OH/methanol (10/90 v/v) to neutralize the reaction mixture. The obtained methoxycarbonyl end-functionalized polyisobutylene is purified by repeated precipitation from hexane into methanol, followed by drying in vacuum.

The hydroxyl end-functional polyisobutylene is obtained by the reduction of methoxycarbonyl group of the above polymer. To a suspension of LiAlH$_4$ (1.51 g, 39.8 mmol) in THF (20 mL) is added a solution of methoxycarbonyl end-functionalized PIB polymer (1.90 g, 0.6 mmol) in THF (20 mL) at $0°$ C. under nitrogen. The resulting solution is stirred at room temperature for 1 hour and refluxed for 50 hours. To the solution is added a solution of 2% H$_2$SO$_4$ (30 ml) at $0°$ C. under nitrogen. Hexane (100 ml) is added after complete addition of H$_2$SO$_4$. The solution is washed with water several times and a dilute sodium bicarbonate aqueous solution. The organic phase is dried over anhydrous sodium sulfate and concentrated by evaporation. The obtained polymer is precipitated from hexane into methanol, followed by drying in vacuum at $50°$ C.

A schematic of the preparation of a methoxycarbonyl end-functional polyisobutylene and subsequent reduction of the methoxycarbonyl group to form the hydroxyl end-functional polyisobutylene is provided below:

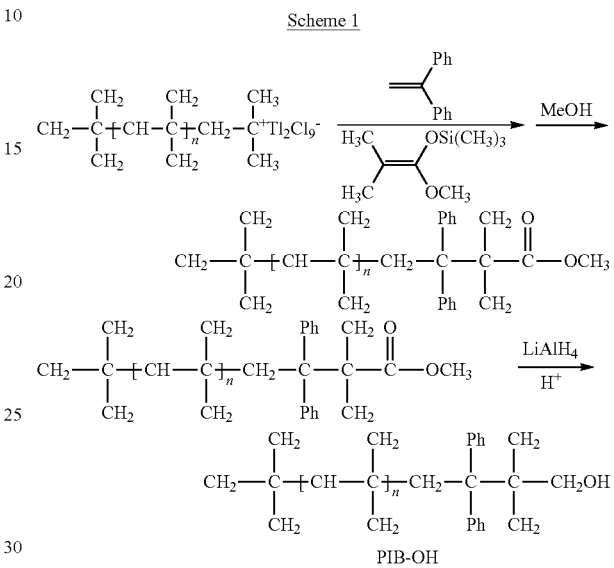

2. Synthesis of Dihydroxyl End-Functional Polyisobutylene Macroinitiator

Polyisobutylene having two hydroxyl end functional groups is synthesized with 5-tert-butyl m-dicumyl chloride as an initiator for living cationic polymerization of polyisobutylene and DTE for the capping reaction in a manner similar to the synthesis of the hydroxyl end functional polyisobutylene described above.

3. Synthesis of Poly(caprolactone-b-isobutylene) Diblock Copolymer.

Hydroxyl end-functional polyisobutylene macroinitiator in toluene, caprolactone, and Sn(Oct)$_2$ (1 equivalent/hydroxyl end group) are placed in a round bottom flask at room temperature under nitrogen. The flask is placed in $120°$ C. oil bath for 24 h with continuous stirring. After 24 h the polymer solution is poured into methanol and the resulting polymer is dried in vacuum. The diblock copolymers are synthesized utilizing polyisobutylene blocks having a Mn of approximately 5.2 kDa and a poly(caprolactone) endblock having a Mn of approximately 14.4 kDa.

4. Synthesis of Poly(caprolactone-b-isobutylene-caprolactone) Triblock Copolymer.

The triblock copolymer is synthesized with ε-caprolactone and dihydroxyl end-functional polyisobutylene as a macroinitiator in a manner similar to the synthesis of the polyisobutylene-polycaprolactone block copolymer described above utilizing polyisobutylene midblocks having a Mn of approximately 36 to 66 kDa and poly(caprolactone) endblocks having a variety of molecular weights, ranging from 2.6 to 18 kDa.

Characterization.

$^1$H NMR spectra are recorded with a Bruker 250 MHz instrument in $CDCl_3$. IR nspectra are measured with a PERKIN ELMER FT-IR spectrophotometer 1720x. Molecular weights and molecular weight distributions of the polymer products of the synthesis steps 1 through 4, above, are measured by a Viscotek GPC system (a Model 250 RI/viscosity detector) using five ultrastyragel columns connected in the following series: 500, $10^3$, $10^4$, $10^5$ and 100 Å. Tetrahydrofuran (THF) is used as the eluent at a flow rate of 1 mL/min. The $M_n$ of the polycaprolactone segment in the copolymers were also calculated by $^1$H NMR spectroscopy from the intensity ratio of the polyisobutylene aromatic end group signal at 7.6~7.7 ppm with the signal of the polycaprolactone methylene group at 4.10 ppm. Differential scanning calorimetry (DSC) is performed with a 2910 Modulated DSC (TA Instruments) using a heating/cooling scan rate of 10° C./min in the temperature range from −100° C. to 200° C.

EXAMPLE 2

Synthesis and Characterization of Poly(Lactic Acid)-Polyisobutylene-Poly(Lactic Acid) Triblock Copolymer Block Copolymer Synthesis.

1. Synthesis of Dihydroxyl End-Functional Polyisobutylene Macroinitiator

Polyisobutylene having two hydroxyl end functional groups is synthesized as an initiator for living cationic polymerization of polyisobutylene. As an alternative to the synthesis method provided above, a dihydroxyl end-functional polyisobutylene macroinitiator is formulated via the preparation of a di-aldehyde-telechelic polyisobutylene.

The di-allyl-terminated polyisobutylene is prepared in drybox. 300 mL of anhydrous hexane, 200 mL of methyl chloride, 40.0 mL of IB, 0.125 mL of DTBP and 0.1982 g of initiator (5-tert-butyl-1,3-bis(2-methoxy-2-propyl) benzene) is mixed up in a 1 L three neck flask equipped with a mechanical stirrer at −80° C. The reaction is started by the addition of 2.5 mL of $TiCl_4$ dissolved in 10 mL of anhydrous hexane. After 1 hour reaction time, 2.5 mL of $TiCl_4$ and 2.5 mL of allyl-trimethyl silane is added. The total reaction time is 2 hours. The reaction is terminated by the addition of 100 mL of prechilled methanol. The solvents are evaporated and the polymer is purified by dissolving twice in hexane (50 mL) and precipitating it with methanol (200 mL). The polymer is dried in vacuum.

A di-epoxy-telechelic polyisobutylene is prepared from the resulting di-allyl-terminated polyisobutylene. Diallyl-PIB (26.1 g) is dissolved in 200 mL of $CH_2Cl_2$. Then, 5.0 g of 3-chloro-perbenzoic acid in 250 mL of $CH_2Cl_2$ is added over a period of 30 minutes during continuous stirring. The mixture is stirred for an additional 6 hours. The polymer is precipitated by the addition of excess of methanol. The crude polymer is dried in vacuum.

The epoxy-terminated polymer (25.6 g) is dissolved in 200 mL of toluene at 110° C. then 0.1 g of zinc bromide is added and the mixture is boiled for 2 hours. The $ZnBr_2$ is filtered off and the solvent is evaporated to create a di-aldehyde-telechelic polyisobutylene. This aldehyde-terminated polyisobutylene (25 g) is dissolved in 200 mL of anhydrous tetrahydrofuran, 1.0 g of $LiAlH_4$ is added and the mixture is boiled overnight. The remaining $LiAlH_4$ is decomposed by the addition of 2 mL of 20% (m/m) $H_2SO_4$. The solvent is evaporated and the polymer is purified by dissolving it in hexane (50 mL) and precipitating with methanol (200 mL).

2. Synthesis of Poly(Lactic Acid)-polyisobutylene-poly(Lactic Acid) Copolymer

In a 100 mL round bottom flask equipped with an oil bath and magnetic stirrer, 7.8 g of the dihydroxyl end-functional polyisobutylene ($M_n$~40 kDa) and 0.25 g of tin octoate is dissolved in 30.4 mL of anhydrous toluene at 100° C. under nitrogen. After complete dissolution (55 minutes), 5.7 g of L,L-lactide is added. The reaction mixture is stirred for 20 hours. The solvent is evaporated (80° C., 20-2 Hgmm).

A schematic of the polymerization of lactic acid using a hydroxyl end-functional polyisobutylene as the macroinitiator is provided below (wherein PIB is polyisobutylene, and PLA is poly(lactic acid):

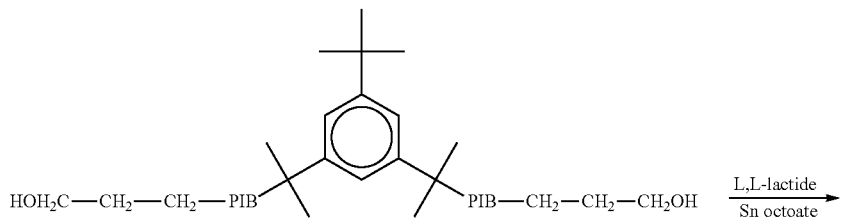

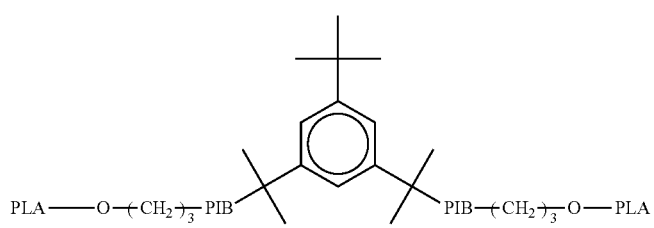

Characterization.

A chromatography column (38×540 mm) is charged with 300 g of Kiesel gel (0.063-0.2 mm) in $CH_2Cl_2$. The column is washed with 600 mL of $CH_2Cl_2$. 13.0 g of crude triblock is dissolved in 130 mL of $CH_2Cl_2$ and loaded on the column. Fractionation into seven fractions verified that fractions 3, 4, 5, 6 are poly(lactic acid)-polyisobutylene-poly(lactic acid) block copolymer, with fractions 1 and 2 having unreacted polyisobutylene homopolymer, and fraction 7 having bimodal distribution, most probably containing the triblock copolymer and the poly(lactic acid) homopolymer.

EXAMPLE 3

Stent Coatings

1. Preparation of Coatings

Solutions are provided that contain 25 wt % tetrahydrofuran (THF), 74 wt % toluene, and 1 wt % solids (paclitaxel and polymer). All solutions are prepared by mixing the paclitaxel and THF until the paclitaxel is thoroughly dissolved, then adding the polymer, followed by the toluene, thoroughly mixing (e.g., overnight), and filtering.

Solutions were made containing the following: (1) 0.25 wt % paclitaxel and 0.75 wt % of a copolymer blend comprising polystyrene-polyisobutylene-polystyrene (0.25 wt %) triblock copolymer (SIBS), as described in United States Patent Application 20020107330 and U.S. Pat. No. 6,545,097 entitled "Drug delivery compositions and medical devices containing block copolymer," and polycaprolactone-polyisobutylene-polycaprolactone (0.50 wt %) triblock copolymer (PCL-PIB-PCL); (2) 0.25 wt % paclitaxel 0.75 wt % of a copolymer blend comprising 0.25 wt % PCL-PIB-PCL and 0.50 wt % SIBS; (3) 0.25 wt % paclitaxel 0.75 wt % of a copolymer blend comprising 0.10 wt % PCL-PIB-PCL and 0.65 wt % SIBS; (4) 0.25 wt % paclitaxel and 0.75 wt % PCL-PIB-PCL (5) 0.25 wt % paclitaxel and 0.75 wt % of poly(lactic acid)-polyisobutylene-poly(lactic acid) triblock copolymer (PLA-PIB-PLA); (6) 0.088 wt % paclitaxel and 0.912 wt % PLA-PIB-PLA, (7) 0.25 wt % paclitaxel and 0.75 wt % of a copolymer blend comprising 0.25 wt % SIBS and 0.50 wt % polycaprolactone-polyisobutylene diblock copolymer (PCL-PIB); (8) 0.25 wt % paclitaxel and 0.75 wt % of a copolymer blend comprising 0.65 wt % SIBS and 0.10 wt % PCL-PIB; (9) 0.25 wt % paclitaxel and 0.75 wt % PCL-PIB; (10) 0.088 wt % paclitaxel and 0.912 wt % SIBS (11) 0.25 wt % paclitaxel and 0.75 wt % SIBS.

Each solution is then placed in a syringe pump and fed to a spray nozzle. A stent is mounted onto a holding device parallel to the nozzle and rotated to ensure uniform coverage. Depending on the spray equipment used, either the stent or spray nozzle can be moved while spraying such that the nozzle moves along the stent while spraying for one or more passes. After a carrier coating is formed in this fashion, the stent is dried, for example, by placing it in a preheated oven for 30 minutes at 65° C., followed by 3 hours at 70° C. Eight stents are formed in this manner for each of the solutions.

2. Paclitaxel Release from Stent Coatings

Figure 2:
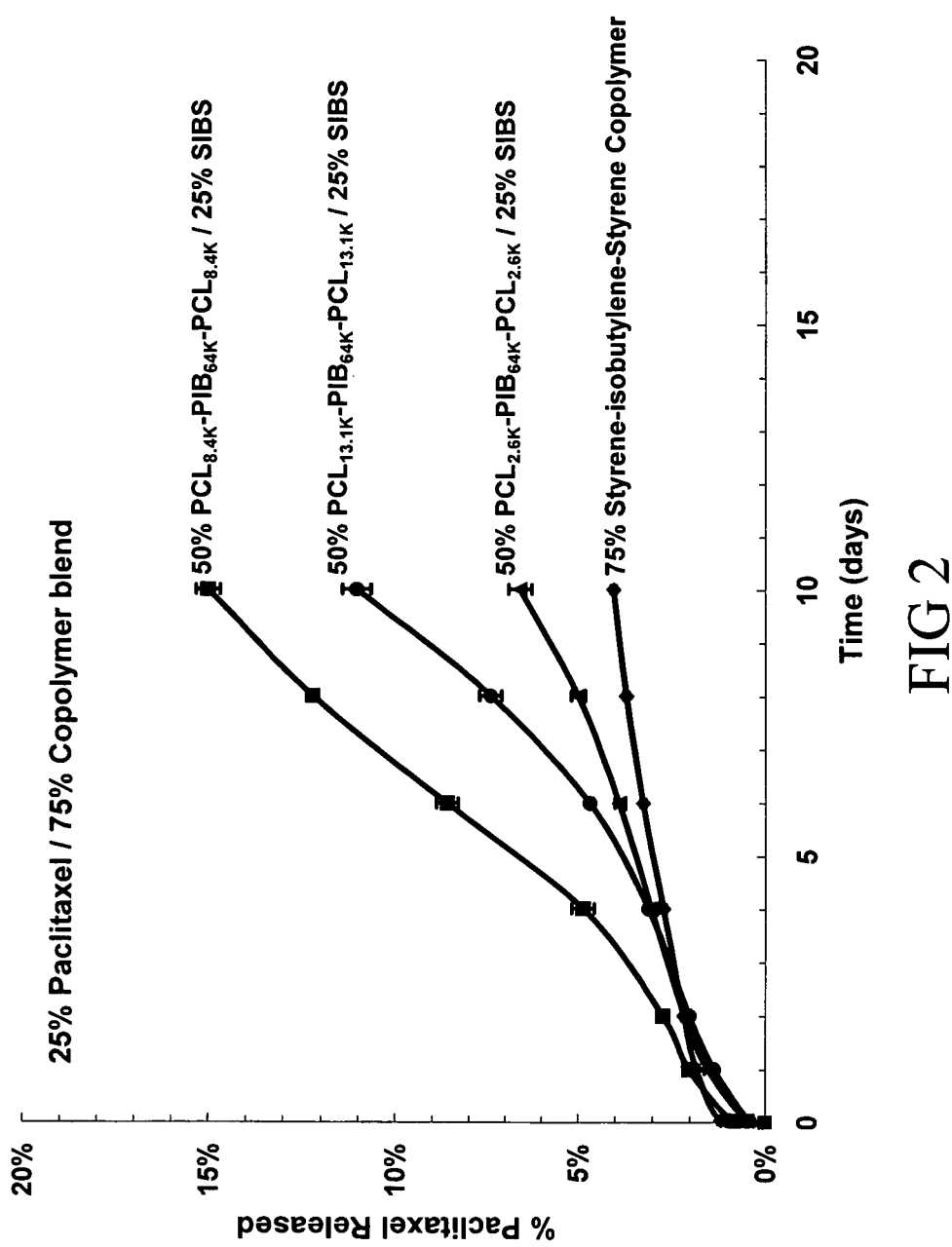
FIGS. 2-7 graphically illustrate kinetic release rate of a therapeutic agent, paclitaxel, as a function of time for stents coated with various polymers and polymer blends.
Figure 3:
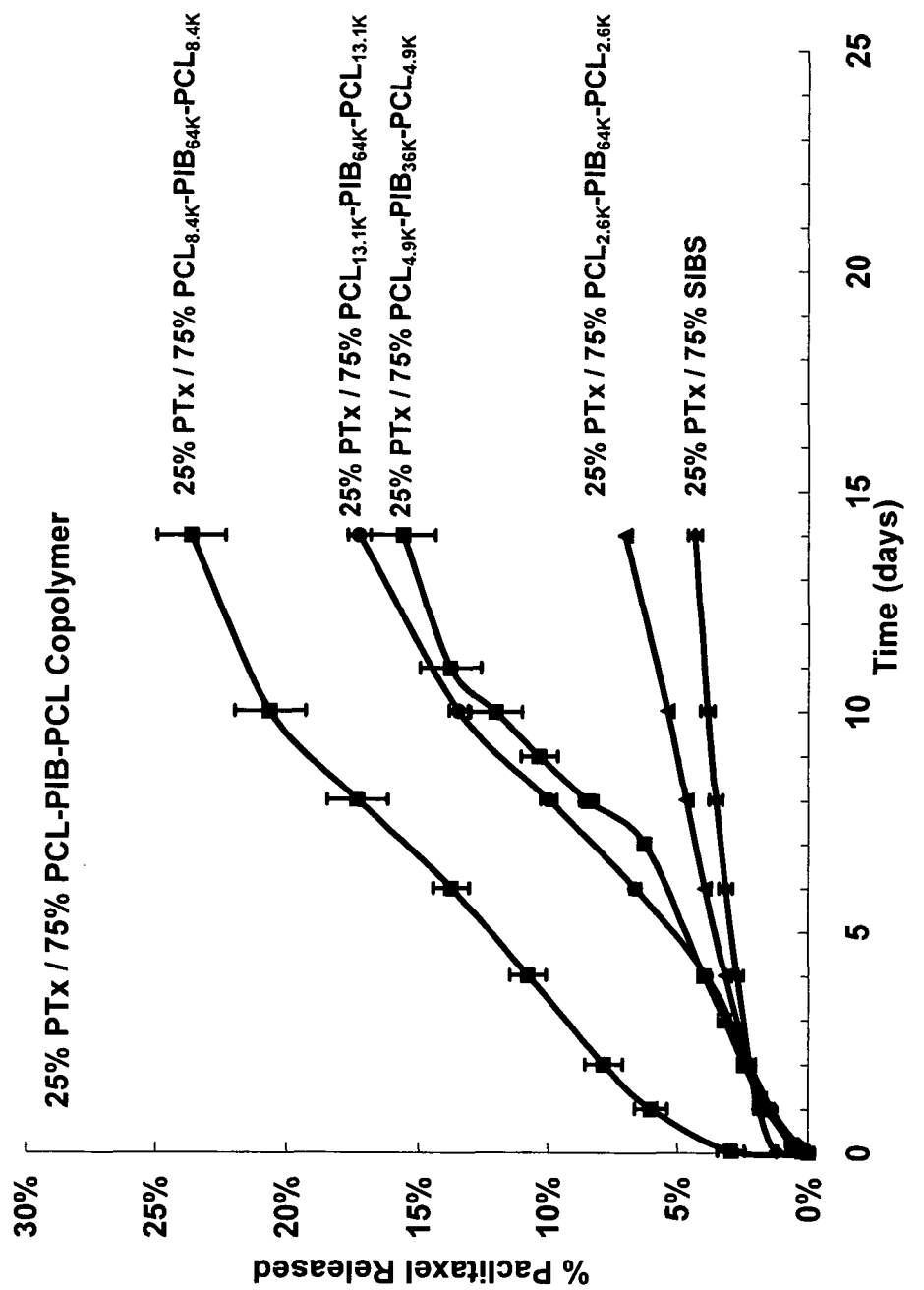
Figure 4:
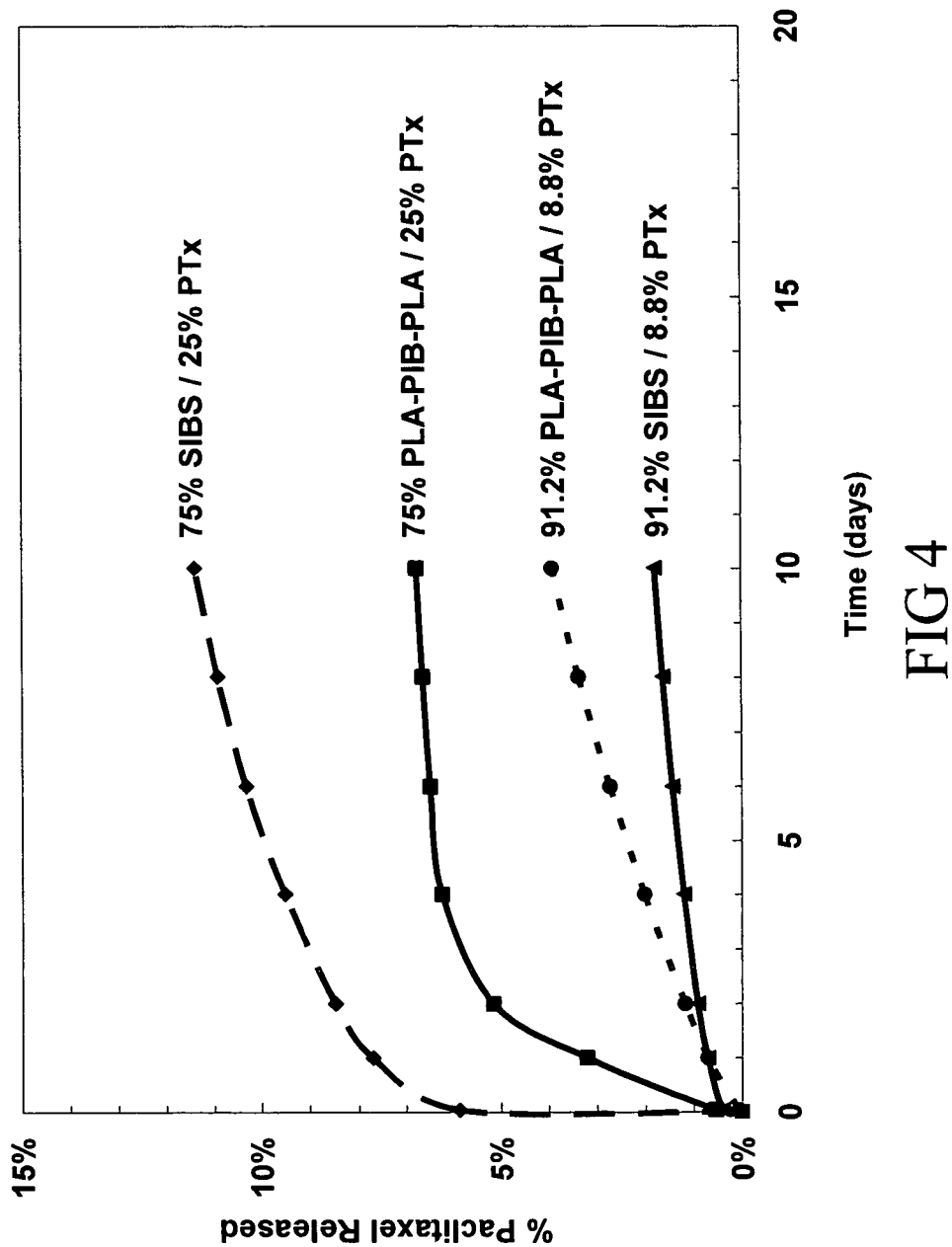
Figure 5:
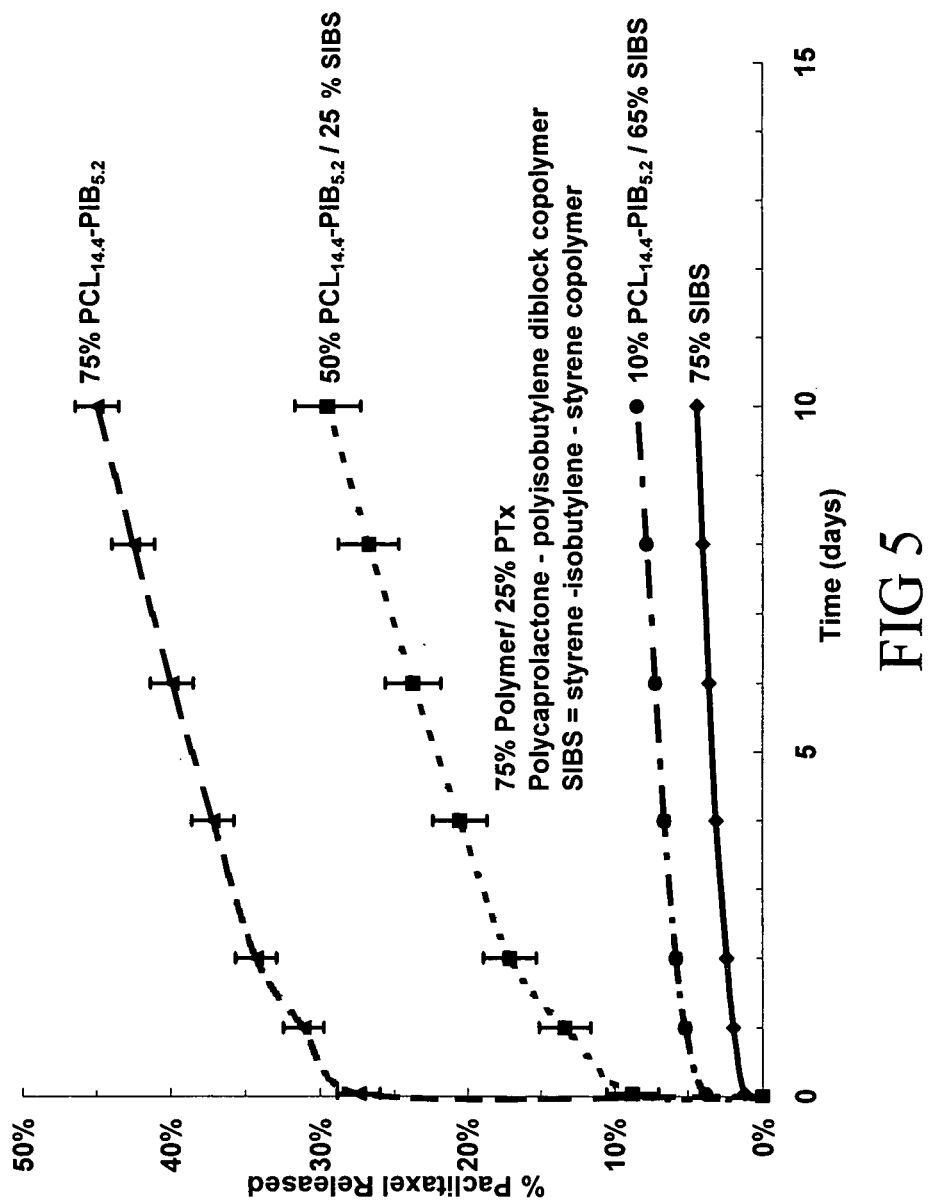
Figure 6:
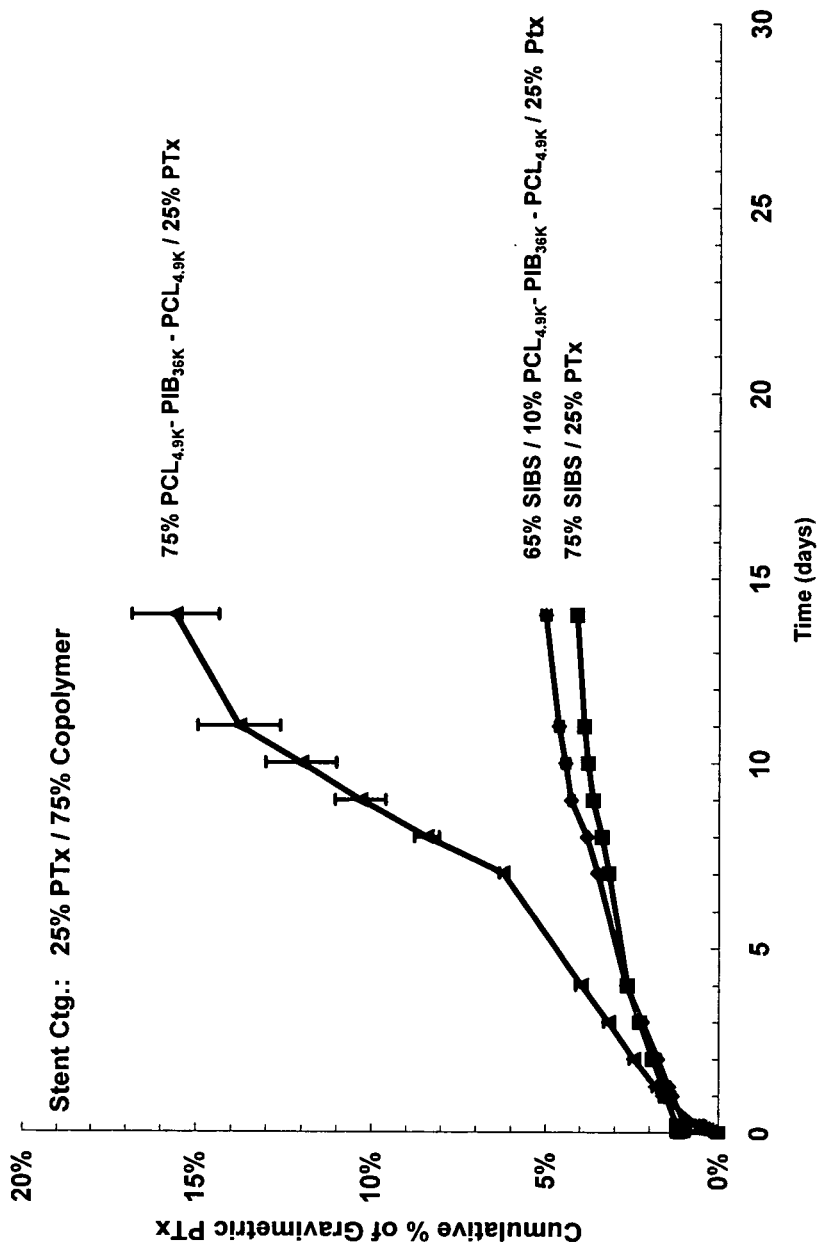
Figure 7:
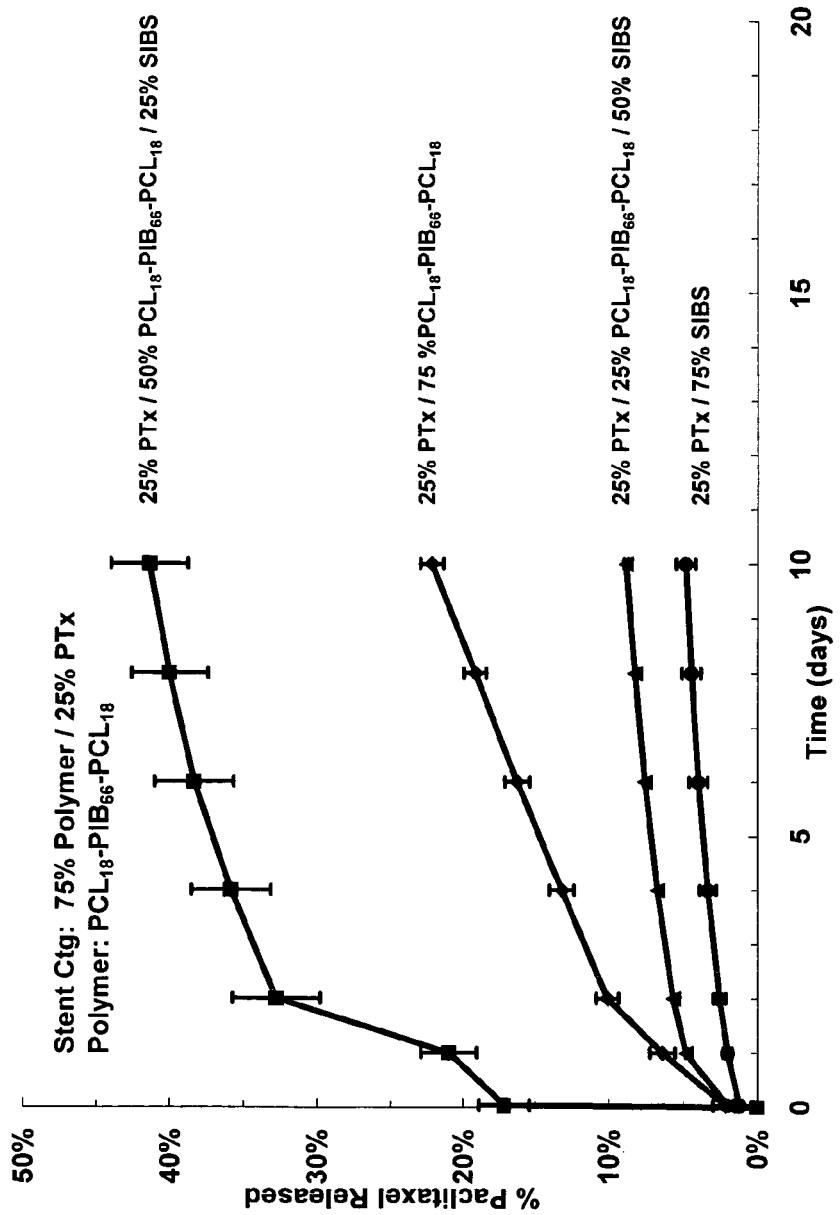

The release of paclitaxel from stent coatings prepared according to the present invention is measured as a function of time. The results, presented as the cumulative release of paclitaxel as a function of time in PBS with 0.5% wt % Tween® 20 (polyoxyethylene(20) sorbitan monolaurate) available from Sigma-Aldrich, are displayed as follows: FIG. 2 graphically illustrates the results obtained for coatings formed using solutions (1) and (11), described above; FIG. 3 graphically illustrates the results obtained for coatings formed using solutions (4) and (11) above; FIG. 4 graphically illustrates the results obtained for coatings formed using solutions (5), (6), (10) and (11), described above; FIG. 5 graphically illustrates the results obtained for coatings formed using solutions (7), (8), (9) and (11), described above; FIG. 6 graphically illustrates the results obtained for coatings formed using solution (3), (4) and (11), described above; and FIG. 7 graphically illustrates the results obtained for coatings formed using solutions (1), (2), (4) and (11), described above.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising a phase separated polymeric region that comprises a block copolymer comprising a biodegradable polymer block, a biostable low $T_g$ elastomeric block and a biostable high $T_g$ elastomeric block and is in the form of a polymeric layer overlying a medical device substrate, said phase separated polymeric region comprising (a) a plurality of biostable polymeric phases and (b) a biodisintegrable polymeric phase of nanoscale dimensions that undergoes biodisintegration in vivo, such that said phase separated polymeric region becomes a nanoporous polymeric region when the device is introduced into a patient as a result of the in vivo biodisintegration of the biodisintegrable polymeric phase.

2. The implantable or insertable medical device of claim 1, wherein said biodisintegrable polymeric phases and said biostable polymeric phase are co-continuous in at least a portion of said polymeric region.

3. The implantable or insertable medical device of claim 1, wherein said biodisintegrable polymeric phase extends throughout the thickness of the polymeric region in at least a portion of said polymeric region.

4. The implantable or insertable medical device of claim 1, wherein said medical device is selected from a guide wire, a balloon, a vena cava filter, a stent, a stent graft, a vascular graft, a cerebral aneurysm filler coil, a myocardial plug, a heart valve, a vascular valve, and a tissue engineering scaffold.

5. An implantable or insertable medical device comprising a phase separated polymeric region in the form of a polymeric layer overlying a medical device substrate, said phase separated polymeric region comprising (a) a biostable polymeric phase and (b) a biodisintegrable polymeric phase of nanoscale dimensions that undergoes biodisintegration in vivo, such that said phase separated polymeric region becomes a nanoporous polymeric region in vivo that comprises a network of interconnected pores extending throughout the polymeric region, and a therapeutic agent disposed beneath or within said polymeric region, wherein the medical device releases the therapeutic agent when the device is introduced into a patient as a result of the in vivo biodisintegration of the biodisintegrable polymeric phase.

6. The implantable or insertable medical device of claim 5, wherein said polymeric layer is disposed over a region comprising said therapeutic agent and wherein the polymeric layer becomes a porous therapeutic-agent-releasing membrane upon in vivo biodisintegration of the biodisintegrable polymeric phase.

7. The implantable or insertable medical device of claim 5, wherein said polymeric layer comprises said therapeutic agent.

8. The implantable or insertable medical device of claim 5, wherein said polymeric region is formed by evaporation of solvent from a solution or dispersion that comprises said solvent and dissolved polymer.

9. The implantable or insertable medical device of claim 8, wherein said solution is sprayed on the surface of the medical device.

10. The implantable or insertable medical device of claim 8, wherein said solution further comprises a therapeutic agent in dissolved or dispersed form.

11. The implantable or insertable medical device of claim 5, wherein said biodisintegrable polymeric phase and said biostable polymeric phase are co-continuous in at least a portion of said polymeric region.

12. The implantable or insertable medical device of claim 5, wherein said biodisintegrable polymeric phase extends throughout the thickness of the polymeric region in at least a portion of said polymeric region.

13. The implantable or insertable medical device of claim 5, wherein said medical device is selected from a guide wire, a balloon, a vena cava filter, a stent, a stent graft, a vascular graft, a cerebral aneurysm filler coil, a myocardial plug, a heart valve, a vascular valve, and a tissue engineering scaffold.

14. The implantable or insertable medical device of claim 5, wherein said polymeric region comprises (a) a biostable homopolymer or copolymer and (b) a biodisintegrable homopolymer or copolymer.

15. The implantable or insertable medical device of claim 5, wherein said polymeric region comprises (a) a biostable homopolymer and (b) a biodisintegrable homopolymer or copolymer.

16. The implantable or insertable medical device of claim 15, wherein said biostable homopolymer comprises a monomer selected from acrylate monomers, methacrylate monomers, alkylene monomers, halogenated alkylene monomers, vinyl ether monomers, vinyl aromatic monomers, and organo-siloxane monomers.

17. The implantable or insertable medical device of claim 14, wherein said polymeric region comprises (a) a biostable copolymer and (b) a biodisintegrable homopolymer or copolymer.

18. The implantable or insertable medical device of claim 17, wherein said biostable copolymer comprises one or more monomers selected from acrylate monomers, methacrylate monomers, alkylene monomers, halogenated alkylene monomers, vinyl ether monomers, vinyl aromatic monomers, and organo-siloxane monomers.

19. The implantable or insertable medical device of claim 18, wherein said biostable copolymer comprises a vinyl aromatic monomer and an alkylene monomer.

20. The implantable or insertable medical device of claim 14, wherein said polymeric region comprises (a) a biostable homopolymer or copolymer and (b) a biodegradable homopolymer.

21. The implantable or insertable medical device of claim 20, wherein said biodegradable homopolymer is a biodegradable polyester homopolymer.

22. The implantable or insertable medical device of claim 14, wherein said polymeric region comprises (a) a biostable homopolymer or copolymer and (b) a biodegradable copolymer.

23. The implantable or insertable medical device of claim 22, wherein said biodegradable copolymer is a biodegradable polyester copolymer.

24. The implantable or insertable medical device of claim 14, wherein said polymeric region comprises (a) a biostable homopolymer or copolymer and (b) a biodissolvable homopolymer or copolymer.

25. The implantable or insertable medical device of claim 24, wherein said biodissolvable homopolymer or copolymer comprises an alkylene oxide monomer or a combination of alkylene oxide monomers.

26. The implantable or insertable medical device of claim 5, wherein said polymeric region comprises a block copolymer that comprises a biostable polymer block and a biodegradable polymer block.

27. The implantable or insertable medical device of claim 1, wherein said biostable low Tg block is a homopolymer or copolymer block that comprises one or more monomers selected from alkene monomers, halogenated alkene monomers, acrylic monomers, methacrylic monomers, vinyl ether monomers, cyclic ether monomers, and siloxane monomers.

28. The implantable or insertable medical device of claim 27, wherein said biostable high Tg block is a homopolymer or copolymer block that comprises one or more monomers selected from vinyl aromatic monomers, acrylic monomers and methacrylic monomers.

29. The implantable or insertable medical device of claim 27, wherein said biodegradable polymer block is a biodegradable polyester homopolymer or copolymer block.

30. The implantable or insertable medical device of claim 28, wherein said biodegradable polymer block is a biodegradable polyester homopolymer or copolymer block.

31. The implantable or insertable medical device of claim 1, wherein said biostable low Tg block is a homopolymer or copolymer block that comprises one or more monomers selected from alkene monomers.

32. The implantable or insertable medical device of claim 31, wherein said biostable high Tg block is a homopolymer or copolymer block that comprises one or more monomers selected from vinyl aromatic monomers and alkyl methacrylate monomers.

33. The implantable or insertable medical device of claim 31, wherein said biodegradable polymer block is a biodegradable polyester homopolymer or copolymer block.

34. The implantable or insertable medical device of claim 32, wherein said biodegradable polymer block is a biodegradable polyester homopolymer or copolymer block.

35. The implantable or insertable medical device of claim 1, wherein said biostable low Tg block is a polyisobutylene block.

36. The implantable or insertable medical device of claim 35, wherein said biostable high Tg block is a polystyrene block.

37. The implantable or insertable medical device of claim 36, wherein said biodegradable polymer block is a polycaprolactone, polylactide, polyglycolide or poly(lactide-co-glycolide) block.

38. The implantable or insertable medical device of claim 1, wherein said block copolymer comprises a biostable low Tg elastomeric midblock, two biodegradable polymer end blocks, and two biostable high Tg elastomeric block between the midblock and the endblocks.

39. The implantable or insertable medical device of claim 1, wherein the in vivo biodisintegration of the biodisintegrable polymeric phase produces a network of interconnected pores that extend throughout the polymeric region.

40. The implantable or insertable medical device of claim 1, comprising a therapeutic agent disposed beneath or within said polymeric region, wherein the medical device releases the therapeutic agent when the device is introduced into a patient as a result of the in vivo biodisintegration of the biodisintegrable polymeric phase.

41. The implantable or insertable medical device of claim 40, wherein said polymeric layer is disposed over a region comprising said therapeutic agent and wherein the polymeric layer becomes a porous therapeutic-agent-releasing membrane upon in vivo biodisintegration of the biodisintegrable polymeric phase.

42. The implantable or insertable medical device of claim 40, wherein said polymeric layer comprises said therapeutic agent.

43. The implantable or insertable medical device of claim 42, wherein the therapeutic agent is concentrated within the biodisintegrable polymeric phase.

44. The implantable or insertable medical device of claim 7, wherein the therapeutic agent is concentrated within the biodisintegrable polymeric phase.

45. The implantable or insertable medical device of claim 5, wherein said phase separated polymeric region comprises a block copolymer comprising a biodegradable polymer block, a biostable low Tg elastomeric block and a biostable high Tg elastomeric block.

46. The implantable or insertable medical device of claim 45, wherein said biostable low Tg block is a homopolymer or copolymer block that comprises one or more monomers selected from alkene monomers, halogenated alkene monomers, acrylic monomers, methacrylic monomers, vinyl ether monomers, cyclic ether monomers, and siloxane monomers.

47. The implantable or insertable medical device of claim 46, wherein said biostable high Tg block is a homopolymer or copolymer block that comprises one or more monomers selected from vinyl aromatic monomers, acrylic monomers and methacrylic monomers.

48. The implantable or insertable medical device of claim 46, wherein said biodegradable polymer block is a biodegradable polyester homopolymer or copolymer block.

49. The implantable or insertable medical device of claim 47, wherein said biodegradable polymer block is a biodegradable polyester homopolymer or copolymer block.

50. The implantable or insertable medical device of claim 45, wherein said biostable low Tg block is a homopolymer or copolymer block that comprises one or more monomers selected from alkene monomers.

51. The implantable or insertable medical device of claim 50, wherein said biostable high Tg block is a homopolymer or copolymer block that comprises one or more monomers selected from vinyl aromatic monomers and alkyl methacrylate monomers.

52. The implantable or insertable medical device of claim 50, wherein said biodegradable polymer block is a biodegradable polyester homopolymer or copolymer block.

53. The implantable or insertable medical device of claim 51, wherein said biodegradable polymer block is a biodegradable polyester homopolymer or copolymer block.

54. The implantable or insertable medical device of claim 45, wherein said biostable low Tg block is a polyisobutylene block.

55. The implantable or insertable medical device of claim 54, wherein said biostable high Tg block is a polystyrene block.

56. The implantable or insertable medical device of claim 55, wherein said biodegradable polymer block is a polycaprolactone, polylactide, polyglycolide or poly(lactide-co-glycolide) block.

57. The implantable or insertable medical device of claim 45, wherein said block copolymer comprises a biostable low Tg elastomeric midblock, two biodegradable polymer end blocks and two biostable high Tg elastomeric block between the midblock and the endblocks.

\* \* \* \* \*

UNITED STATES PATENT AND TRADEMARK OFFICE
CERTIFICATE OF CORRECTION

| | |
|---|---|
| PATENT NO. | : 8,535,702 B2 |
| APPLICATION NO. | : 11/048616 |
| DATED | : September 17, 2013 |
| INVENTOR(S) | : Richard et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2124 days.

Signed and Sealed this
Eleventh Day of August, 2015

Michelle K. Lee
*Director of the United States Patent and Trademark Office*